US010760611B2

(12) United States Patent
Oginski et al.

(10) Patent No.: US 10,760,611 B2
(45) Date of Patent: Sep. 1, 2020

(54) ROTATABLE CONNECTION HAVING ROTATIONAL ANGLE LIMITATION

(71) Applicant: Ondal Medical Systems GmbH, Hünfeld (DE)

(72) Inventors: Stefan Oginski, Fulda (DE); Ronny Bauditz, Suhl (DE); Andreas Göbel, Eiterfeld (DE); Annika Euler, Hünfeld (DE)

(73) Assignee: ONDAL MEDICAL SYSTEMS GMBH, Hünfeld (DE)

( * ) Notice: Subject to any disclaimer, the term of this patent is extended or adjusted under 35 U.S.C. 154(b) by 94 days.

(21) Appl. No.: 14/695,350

(22) Filed: Apr. 24, 2015

(65) Prior Publication Data

US 2015/0366627 A1 Dec. 24, 2015

(30) Foreign Application Priority Data

Apr. 24, 2014 (EP) .................................... 14001481

(51) Int. Cl.
*F16C 11/04* (2006.01)
*F16C 11/10* (2006.01)
(Continued)

(52) U.S. Cl.
CPC .............. *F16C 11/04* (2013.01); *A61B 90/50* (2016.02); *F16C 11/10* (2013.01); *F16M 11/08* (2013.01);
(Continued)

(58) Field of Classification Search
CPC ......... A61B 90/50; A61B 19/26; F16C 11/04; F16C 11/10; F16M 11/08; F16M 11/2014;
(Continued)

(56) References Cited

U.S. PATENT DOCUMENTS

| 1,634,922 A | 7/1927 | Stubblebine et al. |
| 3,133,743 A | 5/1964 | Mullin |

(Continued)

FOREIGN PATENT DOCUMENTS

| CN | 102762877 | 2/2016 |
| DE | 3808327 | 9/1988 |

(Continued)

OTHER PUBLICATIONS

EP 14001479, Oct. 12, 2014, European Search Report.
U.S. Appl. No. 16/379,233, filed Apr. 9, 2019, Oginski et al.
U.S. Appl. No. 16/380,064, filed Apr. 10, 2019, Oginski et al.

*Primary Examiner* — Christopher Garft
(74) *Attorney, Agent, or Firm* — Workman Nydegger

(57) ABSTRACT

A rotatable connection for a mounting device for arrangement in an operating room, the rotatable connection includes an adjustable stop mechanism, which can be disposed between a first connection component and a second connection component, and is configured to define at least two different relative rotational angles of the connection components relative to each other or at least two different ranges or rotation. The adjustable stop mechanism includes at least one stop device having a respective counterstop, which is axially disposed between a first part and a second part that are each mounted in a torsion-proof manner. The at least one stop device is configured to define the different relative rotational angles or ranges of rotation by way of the respective counterstop. The invention further relates a support system or a mounting device comprising such a rotatable connection, and to a method for setting the adjustable stop mechanism.

17 Claims, 10 Drawing Sheets

(51) Int. Cl.
  *F16M 11/20* (2006.01)
  *F16M 13/02* (2006.01)
  *F16M 11/08* (2006.01)
  *A61B 90/50* (2016.01)

(52) U.S. Cl.
  CPC ...... *F16M 11/2014* (2013.01); *F16M 13/027* (2013.01); *F16C 2316/10* (2013.01); *Y10T 403/32549* (2015.01)

(58) Field of Classification Search
  CPC ............ F16M 13/027; F16M 2200/024; Y10T 403/32549; Y10T 403/32557; Y10T 403/32975; Y10T 403/32983
  USPC ........ 248/288.11, 477, 125.8, 131, 415, 425, 248/167, 183.1, 186.1–186.2, 282.1, 248/289.11; 403/91–94, 97, 99, 102
  See application file for complete search history.

(56) References Cited

U.S. PATENT DOCUMENTS

| | | | |
|---|---|---|---|
| 3,713,618 A | 1/1973 | Hendrickson et al. | |
| 4,303,135 A | 12/1981 | Benoit | |
| 4,587,908 A | 5/1986 | DeBruyn | |
| 4,673,154 A | 6/1987 | Karapita | |
| 4,772,246 A | 9/1988 | Wenzel | |
| 4,938,094 A | 7/1990 | Cochard | |
| 5,123,768 A * | 6/1992 | Franklin | A46B 5/0075 403/84 |
| 5,685,661 A | 11/1997 | Marka et al. | |
| 5,720,570 A | 2/1998 | Cole et al. | |
| 6,030,103 A | 2/2000 | Gampe et al. | |
| 6,079,949 A * | 6/2000 | Litvin | F04D 29/601 248/292.12 |
| 6,226,068 B1 | 5/2001 | Arcykiewicz et al. | |
| 6,234,259 B1 | 5/2001 | Kuckes et al. | |
| 6,471,363 B1 | 10/2002 | Howell et al. | |
| 6,633,328 B1 | 10/2003 | Byrd et al. | |
| 6,698,704 B2 | 3/2004 | Kuhn | |
| 6,817,585 B2 | 11/2004 | Wagner et al. | |
| 6,866,410 B2 | 3/2005 | Jesurun et al. | |
| 6,899,442 B2 | 5/2005 | Howell et al. | |
| 7,216,726 B2 | 5/2007 | Swietlik et al. | |
| 7,452,088 B2 | 11/2008 | Brester et al. | |
| 7,455,328 B2 | 11/2008 | Chelchowski et al. | |
| 7,559,518 B2 | 7/2009 | Ye | |
| 7,591,446 B2 | 9/2009 | Istas et al. | |
| 7,635,234 B2 | 12/2009 | Schindler et al. | |
| 7,726,823 B2 | 6/2010 | Rus et al. | |
| 7,753,330 B2 | 7/2010 | Brief | |
| 7,938,205 B2 | 5/2011 | Puttmann | |
| 8,056,874 B2 | 11/2011 | Goodwin et al. | |
| 8,070,331 B2 | 12/2011 | Gull et al. | |
| 8,209,816 B2 | 7/2012 | Heger et al. | |
| 8,262,311 B2 | 9/2012 | Trice | |
| 8,591,444 B2 | 11/2013 | Bejarano et al. | |
| 9,022,339 B2 | 5/2015 | Borg et al. | |
| 9,280,037 B2 | 3/2016 | Leblanc et al. | |
| 9,719,560 B2 | 8/2017 | Dreizler | |
| 9,869,343 B2 | 1/2018 | Oginski et al. | |
| 10,247,352 B2 | 4/2019 | Oginski et al. | |
| 10,253,806 B2 | 4/2019 | Oginski et al. | |
| 10,260,673 B2 | 4/2019 | Oginski et al. | |
| 2005/0006542 A1 | 1/2005 | Henning et al. | |
| 2005/0121578 A1* | 6/2005 | Asamarai | F16M 11/2064 248/284.1 |
| 2005/0242261 A1 | 11/2005 | Brahler et al. | |
| 2006/0285915 A1* | 12/2006 | Dellach | F16C 11/10 403/92 |
| 2009/0072106 A1 | 3/2009 | Zheng | |
| 2009/0213596 A1 | 8/2009 | Gull et al. | |
| 2009/0245924 A1 | 10/2009 | Whitling et al. | |
| 2011/0314637 A1 | 12/2011 | Bejarano et al. | |
| 2012/0014744 A1* | 1/2012 | Lin | F16C 11/10 403/91 |
| 2012/0059274 A1 | 3/2012 | Zoth et al. | |
| 2012/0228454 A1* | 9/2012 | Kronung | F16C 11/10 248/288.11 |
| 2013/0189019 A1* | 7/2013 | Kotula | F16M 11/048 403/84 |
| 2014/0105670 A1* | 4/2014 | Plomteux | F16C 11/103 403/83 |
| 2014/0314538 A1 | 10/2014 | Carter et al. | |
| 2015/0308611 A1 | 10/2015 | Oginski et al. | |
| 2016/0102702 A1* | 4/2016 | Lang et al. | B60R 1/00 248/479 |
| 2016/0102802 A1 | 4/2016 | Oginski et al. | |
| 2016/0281915 A1 | 9/2016 | Bowman et al. | |
| 2017/0304022 A1 | 10/2017 | Oginski et al. | |
| 2017/0332977 A1 | 11/2017 | Dalhoff et al. | |
| 2018/0106291 A1 | 4/2018 | Oginski et al. | |
| 2020/0158278 A1 | 5/2020 | Daugirdas | |

FOREIGN PATENT DOCUMENTS

| | | |
|---|---|---|
| DE | 4306802 | 8/1994 |
| DE | 102008011129 | 8/2009 |
| EP | 0392303 | 10/1990 |
| EP | 0614037 | 3/1994 |
| EP | 1473473 | 9/2006 |
| EP | 2325541 | 5/2013 |
| EP | 2096349 | 9/2013 |
| EP | 2937617 | 10/2015 |
| EP | 2937618 | 10/2015 |
| EP | 2937619 | 10/2015 |
| FR | 1341061 | 10/1963 |

* cited by examiner

ROTATABLE CONNECTION HAVING ROTATIONAL ANGLE LIMITATION

The present invention relates to a rotatable connection for a mounting device for arrangement in an operating room, comprising an adjustable stop mechanism, which can be disposed between a spindle and a sleeve, which is mounted so as to be rotatable about a rotational axis relative to the spindle, and configured to define at least two different relative rotational angles of the spindle relative to the sleeve, or at least two different ranges of rotation, wherein the adjustable stop mechanism comprises: a first part, in particular in the form of a ring, which can be mounted on the spindle in a torsion-proof manner and comprises at least one stop; and a second part, which can be disposed or is provided in a torsion-proof manner on the sleeve, wherein the first part is mounted rotatably relative to the second part. The present invention relates in particular to a rotatable connection having individual features of claim 1, to a support system or a mounting device having individual features of the corresponding further independent claim, and to a method for setting the adjustable stop mechanism having individual features of the corresponding independent method claim.

Mounting devices, in particular ceiling mounts such as ceiling supply units, monitor mounts or so-called spring arms or central axes, typically have one or more carriers, which are rigidly disposed in relation to a vertical position or height-adjustable and by way of which medical equipment attached thereto can be moved and positioned, for example in an operating room, and in particular also in an intensive care unit. Supply units are frequently installed on the mounts, by way of which medical-electrical devices can be supplied with the necessary media during surgery, for example. The carriers define an operating range of the medical equipment, within which the medical equipment is positioned. The carriers can usually be rotated at least about at least one rotatable connection, in particular a pivot joint. Optionally, the carriers are also height-adjustable and/or disposed so as to pivot with respect to the height about an at least approximately horizontally oriented axis.

In many cases, a rotary motion of individual carriers, be it an absolute rotary motion or a rotary motion relative to another carrier, is to be limited to a predefined angle. It is thus possible to avoid, for example, that a carrier is rotated by more than 360° with respect to another carrier and lines that are run in the carrier are twisted, pinched or even torn off. A rotational angle limitation can be provided in the form of a stop, for example, against which a carrier strikes at a certain rotation angle, 300°, for example. The stop can be fixedly installed on the carrier, for example, in particular in the form of a safety pin that is introduced in the radial direction. The stop specifies a predefined rotational angle. While such rotational angle limitation can ensure that a maximum rotational angle is not exceeded, it usually also has the disadvantage that the freedom of movement of the mount is limited, which is to say that, for example, a supply unit of the mount cannot be disposed any longer in arbitrary positions. The operating range of the mount is limited, in particular without consideration of a certain spatial situation. It is therefore necessary in each individual case to consider by what stop the rotational angle limitation can or should be defined. However, the correct design of the rotational angle limitation, in particular adequate positioning of the stop, can already cause difficulties in the production a particular mount, in particular when the location at which the respective mount is to be used has not been clarified. Rotational angle limitations by way of which a rotational angle or a rotational position can be subsequently adapted are therefore practical.

A device having a settable rotational angle is known from EP 2 325 541 B1. EP 2 325 541 B1 describes a two-part adjustable stop mechanism, in which an annular part can be selectively positioned on the outside around a periphery of a first carrier or a joint of a first carrier, and the annular part has a plurality of recesses or protrusions on the end face, by way of which it can be disposed in varying rotational angle positions relative to the first carrier in a simple manner. A stop is furthermore provided on the annular part, against which a second carrier can strike. A rotational angle of the two carriers relative to each other can be set by way of the annular part. The stop mechanism is disposed within a collar of the second carrier. By the engagement of a tool in a circumferential groove on an outer lateral surface of the annular part, the annular part can be raised so as to position the annular part relative to the first carrier in a desired rotational angle position. Moreover, a further annular part is provided on the first carrier, which can be positioned relative to the annular part. The two annular parts are disposed within the collar and are surrounded and covered radially on the outside by the collar. A safety pin, which is introduced in the radial direction, is disposed in the collar and engages in a space formed between the two annular parts. The extension of the space is defined in the circumferential direction by the relative rotational position of the first part relative to the second part. The angular range in which the two carriers can be rotated relative to each other can be defined by the extension of the space in the circumferential direction. The stop mechanism is substantially disposed on the first carrier and cooperates with the second carrier via the radially introduced securing pin.

DE 38 08 327 A1 describes a stop mechanism in which a threaded bolt can be displaced in the radial direction in a threaded hole so as to set different rotational angle positions.

It is an object of the present invention to provide a rotatable connection by way of which a rotational angle or rotational (angle) range can be set in a simple manner. The object is in particular also to provide a mounting device having rotational angle limitation in which, thanks to an easily (in particular manually) settable rotatable connection, individual carriers of the mounting device can be flexibly positioned in an operating room.

This object is achieved by a rotatable connection for a mounting device for arrangement in an operating room, comprising an adjustable stop mechanism, which can be disposed between a first connection component (in particular a connection component of the rotatable connection) and a second connection component (in particular a connection component of the rotatable connection), which is mounted rotatably about a rotational axis relative to the first connection component, and configured to define at least two different relative rotational angles of the connection components relative to each other or at least two different ranges of rotation, wherein the adjustable stop mechanism comprises:

a first part, which can be mounted on the first connection component in a torsion-proof manner and comprises at least one stop;

a second part, which is provided or can be disposed on the second connection component in a torsion-proof manner, wherein the first part is mounted rotatably relative to the second part;

wherein the adjustable stop mechanism comprises at least one or two stop devices, each having a counterstop, which is or are disposed axially (which is to say with respect to the axial direction of the rotational axis) between the two parts and thereby can cooperate with the two parts, wherein the respective counterstop corresponds to the stop, and wherein the at least one device is or two devices are configured to define the different relative rotational angles or ranges of rotation by way of the respective counterstop. In this way, a rotatable connection that is easy to set can be provided. The setting can take place by axial displacement and rotation of the at least one stop device, for example, in particular manually. The at least one separate stop device can be disposed in varying rotational positions between the two parts. A pin or securing pin disposed in the radial direction is not necessary. Rather, the components can be positioned in the axial direction with respect to each other. The counterstop or counterstops can be attached in predefined positions on the at least one stop device. It is thus also possible to define different ranges of rotation, which is to say a range of rotation from compass north (which is to say the geographical north direction) by 300° C. clockwise and counterclockwise, for example, or a range of rotation proceeding from compass east by 330°, or a range of rotation from compass north by 370°. In this way, the operating range of a mounting device, for example, can also be adjusted and set with respect to an arrangement close to a wall or in a corner. The (absolute/maximum) value of the rotational angle can be fixedly defined by the geometric design of the stop mechanism, in particular of the stop device, or it can also be set, in particular by displacing at least one stop device relative to the other stop device. The starting point of the rotary motion can be set by offsetting an individual stop device, or by offsetting both stop devices together to the same degree.

By arranging the stop mechanism both on the first connection component and on the second connection component, at least one stop device can be provided, which (in each case) can be displaced in a simple manner between the two connection components and repositioned, in particular by axial displacement of the first part relative to the second part.

The number of components can be minimized by way of a stop device that comprises one or more counterstops. The entire stop mechanism is preferably composed of only three components, in particular the first part, the second part and the stop device.

The connection or mounting of the second part, described as a non-rotatable arrangement, to or on the connection component can be provided by a tongue-and-groove connection, for example, which is to say a joint that defines only a single relative position of the two components with respect to each other. A non-rotatable arrangement, connection or mounting can also comprise an arrangement in which the second part is designed (as once piece) as an integral part of the connection component. In particular, the second part can be integrated into a second connection component designed as a sleeve.

While the first part is preferably mounted on the first connection component in a torsion-proof manner, this preferably only relates to a rotary motion. In other words, the torsion-proof arrangement does not necessarily bring about a predefined axial position. Rather, the first part is preferably mounted on the second connection component in the axial direction, in particular by way of the at least one stop device and/or the second part. The first connection component can preferably be axially positioned on the second connection component in the axial direction, or vice versa, for example by way of a circlip.

A "rotatable connection" shall preferably be understood to mean an arrangement by way of which a rotation of two components with respect to each other by a predefinable angle can be ensured. For example, the rotatable connection is a connection between a sleeve and a spindle, wherein the rotatable connection does not necessarily comprise the sleeve and the spindle, but only the bearings or bearing surfaces provided thereon, for example. The rotatable connection preferably comprises at least one pivot joint or forms part of a pivot joint. A pivot joint shall preferably be understood to mean a joint which allows at least one rotation about one or multiple rotational axes, wherein a translatory degree of freedom can also be implemented. The pivot joint is preferably disposed at the interface between two individual carriers; however, it can also divide a single carrier into multiple sections. The pivot joint can be provided at the interface between a spindle and a sleeve, for example.

A "mounting device" shall preferably be understood to mean a device for holding, arranging in a stationary manner and/or displacing at least one piece of medical equipment, which can be fixedly installed on a wall (in a wall bracket) or a ceiling or on the floor of an operating room or any other room for medical purposes, which is to say a ceiling mount, for example. The mounting device then cannot be displaced completely freely in the operating room, but can be displaced only in a certain operating range, in particular relative to an attachment point or installation point provided on a ceiling or wall of the operating room. The mounting device can be designed as a ceiling supply unit that is installed on a ceiling and can comprise one or more supply consoles, which is or are mounted and positionable on one or two support arms. The mounting device can also be designed as a monitor mount. The mounting device can also be designed as what is known as a spring arm, in particular a spring arm installed on a wall, and comprise a luminaire, for example. The mounting device can also be designed as what is known as a central axis, in particular a central axis installed on a ceiling, and comprise a multitude of support systems, each having at least one carrier on which a monitor or a luminaire, for example, is mounted. However, the mounting device does not necessarily have to be fixedly installed on a wall, but can also be installed on a movable platform. The movable platform can be positioned in the room in a stationary, for example by way of brakes. An adjustable stop mechanism is also useful in this case.

An "adjustable stop mechanism" shall preferably be understood to mean any device that is able to limit a rotational angle and/or a range of rotation of a carrier, in particular relative to a further carrier or relative to a (fictitious) rotational axis fixedly positioned in the room, for example a rotational axis extending through a fixed attachment point on a wall of a room. The adjustable stop mechanism preferably comprises at least one connection, which can also be designed to be form-locked, or is designed for a positive fit. The adjustable stop mechanism can additionally also act in a force-fit manner.

A "range of rotation" shall preferably be understood to mean an angular range in which a carrier can be rotated relative to a further carrier or to a wall. The angular range can be between 90° and 330°, for example. The angular range can have a constant size, but can be defined with respect to different circumferential positions, for example, which is to say from 0° to 300° with respect to a north direction, for example, or from 30° to 330° with respect to an east direction. The range of rotation can be defined by different rotational angle positions, in which counterstops of the stop device(s) can be disposed.

A "first part" shall preferably be understood to mean a part which, in some manner, is coupled in a torsion-proof manner to the rotary motion of the first connection component (a spindle, for example) and preferably cooperates with the first connection component in a form-locked manner. The first part is preferably displaceable relative to the first connection component in the axial direction, preferably in the direction of the rotational axis. A relative displacement with respect to each other in the circumferential direction is blocked, or at least can be blocked starting at a certain rotational angle. The first part can have an annular shape, for example, and can then be referred to as a stop ring, which defines at least one stop. A stop shall preferably be understood to mean some protrusion or projection protruding in the axial direction or ensure an overlap.

A "second part" shall preferably be understood to mean a part which is coupled in a torsion-proof manner to the rotary motion of the second connection component (a sleeve, for example) and cooperates with the second connection component in a form-locked manner, for example, in particular in a rotationally synchronous manner. In other words, the second part is provided on the second connection component in such a way that the second part and the second connection component in any case carry out the same rotary motion. The position of the second part relative to the second connection component is then predefined, and also cannot be changed. The second part can be formed by the second connection component, for example cast on. The second part is preferably provided in a stationary manner on the second connection component, which is to say in an axially fixed manner, which means that it also cannot be displaced in the axial direction relative to the second connection component. The second part is preferably only connected to the second connection component, or is formed thereby, and is decoupled from the first connection component, and cooperates only indirectly with the first connection component by way of the at least one stop device and the first part. The second part can have an annular shape, for example, and can have at least one form-locked contour in the form of teeth, such as a saw tooth contour, in particular at the interface to the stop device. The second part can then be referred to as a toothed ring. Preferably no stops or counterstops that define a range of rotation are disposed on the second part. Such stops are not necessary, in particular since a relative rotary motion between the second part and the at least one stop device does not have to, or should not, take place. The second part is preferably configured to mount the at least one stop device in a rotationally fixed manner in a settable rotational position on the second connection component, so that a stop of the first part can strike against the at least one stop device, so as to transfer a resulting reaction force from the at least one stop device to the second part. In other words, the first part preferably has only an indirect connection to the second part, in particular via the stop device.

A "stop device" shall preferably be understood to mean a part which is configured to provide a counterstop in a stationary position relative to one of the connection components, in particular relative to the second connection component, wherein a (torsional) force exerted on the stop device in the circumferential direction, which is to say a torque, can be transferred between the connection components via the counterstop. The stop device is preferably configured to prevent a direct cooperation between the first and second parts. The at least one stop device is preferably mounted on an intermediate basis between the first and second parts and is configured to transfer a torque between the first part and the second part. The stop device preferably extends around the rotational axis at least in sections, wherein the stop device preferably has an annular shape and is provided peripherally around the rotational axis. The stop device can then be described as an adjusting ring, for example. A counterstop shall preferably be understood to mean some protrusion, projection or a protruding lug.

An arrangement "axially between" the first and second parts shall preferably be understood to mean an arrangement in which the first and second parts are not directly coupled to each other, but only indirectly by way of the stop device. An arrangement "axially between" shall preferably mean that the first part does not have to engage in the second part in the axial direction, but that an engagement or cooperation between the first part and the second part can be ensured (solely) by way of the at least one stop device.

A "rotational angle position" shall preferably be understood to mean a relative rotational position of a stop device with respect to one of the connection components, in particular with respect the second connection component. The rotational angle position can be defined by the relative position of a counterstop. The rotational angle position can also be described with respect to an absolute (horizontal) angle, for example about a (fictitious) vertically oriented rotational axis.

The at least one stop device is preferably configured to transfer a rotational force acting in the circumferential direction, which is exerted on the stop or the counterstop, between the first and second parts, which is to say from the first part to the second part and/or from the second part to the first part. In other words, the at least one stop device is configured to couple the two parts to each other, in particular also to define a certain rotational angle range of the parts relative to each other.

According to one exemplary embodiment, at least one of the stop devices can be positioned in a torsion-proof manner with respect to one of the two parts, in particular with respect to the second part, on one of the two parts in at least two different rotational angle positions. In this way, a starting point of a certain rotational angle range can be set. The counterstop is preferably positioned on the at least one stop device in a stationary manner. The counterstop can be integrally provided on the at least one stop device, which is to say the stop device form a single piece with the counterstop. In this way, it is possible to ensure a lower number of parts or components. It is possible in particular to prevent small adjusting screws or radial pins from being lost. Optionally, the counterstop, or at least one counterstop of a plurality of counterstops, can also be attached to the at least one stop device, for example by way of a screw assembly in the radial or axial direction. This simplifies the setting of a certain rotational angle, for example.

The first part is preferably disposed displaceably along the rotational axis in the axial direction. In this way, the at least one stop device can be easily displaced together with the first part in the axial direction so as to set the range of rotation or rotational angle. It is not necessary to remove any pin engaging in the radial direction, or a collar accommodating the pin, to displace the two parts relative to each other in the axial direction. The first part can be guided by way of a centering device on an inner lateral surface on the first connection component. Optionally, the stop device can be raised without the first part, in particular by previously removing a retaining device (such as a circlip), which can be disposed above the first part and prevent an axial displacement.

The at least one of the at least one stop devices is preferably disposed so as to be displaceable in the axial direction along the rotational axis, in particular together with the first part. In this way, the rotatable connection is easy to set. For example, all that is required is to grab the at least one stop device, and the first part can be axially moved together with the at least one stop device, in particular in an upward direction counter to a gravitational force.

The first part and the at least one or two stop devices are preferably inserted into each other in the axial direction or at least disposed so as to axially overlap each other.

The first part and the second part and the at least one stop device are preferably disposed behind each other in series in the axial direction. In this way, the rotatable connection, in particular the starting point of the rotational angle range, is easy to set, in particular after the first part and the stop device were pushed axially away from each other.

The range of rotation can be easily set by axially displacing the parts and the at least one stop device with respect to each other. A damping element can also be provided in an easy manner between the parts, or one of the parts and the at least one stop device. The arrangement in series behind each other also allows easy installation. An arrangement in series behind each other shall be understood to mean an arrangement in which (apart from a potentially interposed damping element) the first part is seated against the/a stop device, and in which the or a further stop device is seated against the second part.

The at least one stop device is preferably disposed between the two parts in the axial direction, and in the axial direction overlaps the second part in the region of a form-locked contour and in the axial direction overlaps the first part in the region of the stop. By disposing the first part and the at least one stop device in an overlapping manner in the axial direction, the stop mechanism can be provided in the form of a plug-in system having a simple design. It is also possible to ensure good stability of the arrangement, in particular since the first part and the at least one stop device can stabilize each other to prevent tilting, specifically via the inner and/or outer lateral surface of the stop device. The first part is preferably dimensioned and geometrically designed in such a way that the first part, in particular a circumferential inner or outer wall, can be at least partially disposed on the inside or outside around the at least one stop device. This design allows the respective counterstop to be arranged in a ring cavity formed by the first part, whereby the components can mutually secure, stabilize and/or center each other.

The first part and/or the second part preferably extend around the rotational axis at least in sections, wherein the first part and/or the second part preferably have an annular shape and are provided peripherally around the rotational axis.

According to one variant, the first part has an annular shape and comprises two or more stops, which are disposed opposite each other and protrude in the axial direction from a disk of the first part, in particular on an outer lateral surface or a circular ring surface. The first part can have a rotationally symmetrical, in particular a disk-shaped region. A disk shall preferably be understood to mean a substantially planar part, which extends substantially in a plane oriented in the radial direction, having a considerably smaller extension in an axial direction orthogonal to the plane. A design as a disk has the advantage that a sliding surface can be easily provided on a respective end face of the disk.

According to one exemplary embodiment, the first part is configured to couple the stop to at least one respective counterstop of at least two stop devices, in particular by way of axial overlap in the axial direction. Bringing one stop into engagement with multiple counterstops allows high variance in the adjustment of the stop mechanism. The coupling or bringing into engagement can preferably be carried out in such a way that the stop either cooperates separately with each counterstop in individual rotational angle positions or simultaneously with at least two counterstop in the same rotational angle position. This allows a flexible design of the stop mechanism, either with only one stop device, or with two or even more stop devices. In this way, in particular both the range of rotation and the rotational angle can be set or adjusted independently of each other.

The stop can be integrally provided on the first part, which is to say the first part forms a single-piece part together with the stop. In this way, it is possible to ensure a lower number of parts or components. It is possible in particular to prevent small adjusting screws or radial pins from being lost.

According to one exemplary embodiment, the first part is annular and configured to overlap the counterstop of the at least one stop device in the axial direction by way of the stop. This provides the advantage of an adjustment mechanism having a simple design, which can be easily inserted manually in the axial direction, for example.

According to one exemplary embodiment, the first part is designed as a double-wall ring or stop ring, in particular having a U-shaped cross-sectional profile, wherein the stop is designed in the form of a rib extending in the radial direction. As a result, the stop ring is configured to surround the counterstop of the at least one stop device in the axial direction, which it to say to overlap it in the axial direction both radially inside and radially outside. In this way, it is also possible to surround multiple stop devices or counterstops and for these to cooperate with the stop. An angular momentum can thus be transmitted in the same axial section of the rotatable connection, in particular from a tongue-and-groove connection between the first connection component and the annular first part via the stop to the one or multiple counterstops. Bending moments or leverage can thus be kept low. It is also possible to provide a self-contained design having no protruding sections or protrusions whatsoever, which increases the operating safety (for example, reduced risk of crushing or jamming or tilting). In this way, a particularly sleek shape can be achieved even in a radial direction. The annular design of the first part is suitable in particular in connection with a ceiling attachment when space constraints exist in the radial direction. The stop ring preferably has an annularly circumferential U-shaped cross-sectional profile having an at least approximately planar upper face, which connects the legs of the U profile to each other. This geometry, for example, also allows the first part to cooperate in a form-locked manner with a retaining device in a simple way.

The rib preferably connects an inner wall to an outer wall of the ring. The rib is preferably designed as a partition between the inner wall and the outer wall. A partition also has the advantage, for example, that the reaction forces on the stop ring are substantially independent of whether the partition cooperates with one or more counterstops. Angular momentum can be transmitted both to the inner wall and to the outer wall of the stop ring. Bending moments can be kept low. In this way it is also possible to provide a particularly robust arrangement, in particular a robust design of the stop, having advantageous properties with regard to the absorption and transmission of angular moment.

The inner wall and the outer wall of the stop ring are preferably disposed at least approximately parallel to each other and extend at least approximately in the direction of the rotational axis. This design as a parallel double ring can ensure particularly secure engagement of the components in each other and also enables a sleek design. In particular bringing a multitude of stop devices into engagement is simplified.

The counterstop of the at least one stop device is preferably mounted in a ring cavity of the stop ring. Multiple counterstops of multiple stop devices can be brought together in the ring cavity and together can cooperate with the stop. At the same time, each stop device can slide along, or be guided along, a corresponding lateral surface of the stop ring, which improves low-friction operation or prevents the risk of tilting.

According to one exemplary embodiment, the first part and the at least one or two stop devices, and optionally also the second part, for setting individual rotational angle positions or for adjusting the stop mechanism in the axial direction can be axially disposed or axially positioned or mounted on the second connection component. In the axial direction, at least the first part and the stop devices are preferably positioned axially on the second connection component solely based on the weight. This free arrangement (without additional fastening means) can provide a stop mechanism that is particularly easy to set or adjust.

According to one exemplary embodiment, the adjustable stop mechanism has a respective form-locked contour at four interfaces, in particular at interfaces provided at the axial end faces. A component of the adjustable stop mechanism, in particular a lower adjusting ring, preferably has a form-locked contour on both sides. In this way, high variability and simple handling can be ensured with a small number of components (specifically three components: upper adjusting ring, lower adjusting ring and second part or toothed ring).

According to one exemplary embodiment, the at least one stop device is disposed in such a way that a torsion-proof arrangement of the at least one stop device on the second part is ensured (in particular exclusively) by a weight or gravitational force acting on the at least one stop device. For this purpose, only a displacement of the at least one stop device counter to a weight acting on the at least one stop device must be carried out, in particular together with the first part, to adjust the stop mechanism. It is not necessary to remove any radially introduced retaining pins or screws. The first part can rather be axially secured by way of a retaining ring.

According to one exemplary embodiment, the second part has a form-locked contour for defining the individual rotational angle positions, in particular on an upper face pointing in the axial direction. The at least one stop device or one of the stop devices has a corresponding form-locked contour, in particular on a lower face pointing in the axial direction toward the second part or second connection component. In this way an easily accessible plug connection can be provided, by way of which the stop mechanism can be set or adjusted.

A form-locked contour shall preferably be understood to mean teeth or a toothed contour, or a contour having regular protrusions or projections. The shape of an individual tooth is substantially arbitrary. The individual tooth preferably has the shape of a cuboid or, as seen in the cross-section, the shape of a rectangle. The form-locked contour is not necessarily exclusively form-locked, but can also be form-fit. The form-locked contour is preferably not integrally bonded to ensure that the at least one counterstop can be reversibly positioned with arbitrary frequency in varying rotational angle positions.

The form-locked contour of the second part is preferably accessible in an axial direction at least approximately parallel to the rotational axis in such a way that the corresponding form-locked contour of the corresponding stop device can be plugged onto the second part in the axial direction. This simplifies both the installation and the setting.

The form-locked of the second part and the form-locked contour of the at least one stop device are preferably each designed as a toothed ring, wherein teeth of the toothed ring preferably protrude in an axial direction at least approximately parallel to the rotational axis. A toothed ring shall preferably be understood to mean a contour that is designed to be rotation-symmetrical with respect to the rotational axis and has a plurality of individual teeth, in which the teeth are disposed at a uniform distance from each other. The design as a toothed ring offers the advantage of small adjustment increments, for example, since an increasing number of teeth allows a finer definition of the starting point of the rotational angle range, such as in 10° increments.

According to a special exemplary embodiment, the first part and at least one stop device together form a (pivot) bearing, in particular a sliding bearing. The first part is then seated on the at least one stop device, or on at least one of the stop devices, in particular on an annular surface section of the stop device, either directly or indirectly via a retaining device. The first part can thus be displaced with low friction relative to the at least one stop device or the second part, even if a normal force acts on the contact surface between the first part and the at least one stop device. The normal force, however, does not have to be large, because it can correspond to the weight of the first part, for example, A smooth rotatable connection can be provided by the bearing, and the cooperation of the individual components of the rotatable connection can be optimized. The at least one stop device is preferably disposed between the first part and the second part in such a way that the first part is only in contact with the at least one stop device, either directly or at least partially indirectly in conjunction with a retaining device, but without having contact with the second part. The second part, in turn, is only in contact with the at least one stop device and the second connection component. In other words, the first part cooperates with the second part (preferably only) by way of the at least one stop device.

Optionally a sliding surface can also be provided by a retaining ring, in particular by a retaining ring mounted on the second part or second connection component in a predefined axial position, or by a retaining ring mounted in a groove on the first connection component.

In the event that a retaining device is provided, the (pivot) bearing can also be formed between the retaining device and the stop device and/or between the first part and the retaining device, depending on whether a relative movement is to take place between the retaining device and the first part. The retaining device is preferably fixed in a predetermined position on the first part in a force-fit and/or form-locked manner (in particular plugged into the first part in the radial direction) and axially engages between the first part and the (respective) stop device, so that the relative movement between the retaining device and the stop device takes place, but not between the retaining device and the first part.

The lower face of the first part preferably has an abutment surface on which the first part can be slideably rotated relative to the stop device. This abutment surface or sliding surface is preferably designed in an annular circumferential manner. According to one variant, such an abutment surface or sliding surface can also be provided by a/the retaining device.

According to one exemplary embodiment, the first part has a sliding surface that is provided on an end face, in particular on an end face pointing toward the (respective) at least one stop device, and is configured to slideably rotate together with the sliding surface on the at least one stop device. Moreover, the (respective) stop device can have a sliding surface that is provided on an end face, in particular on an end face pointing toward the first part or away from the second connection component, and configured to mount the first part, by way of the sliding surface, for a sliding rotary motion about the rotational axis. The sliding surface of the first part and/or the sliding surface of the at least one stop device can preferably have a completely circumferential design as a circular ring surface, for example, or only in sections. In this way, the bearing for the second part can be provided in a simple and cost-effective manner. Due to the planar seating on the at least one stop device, a robust stop mechanism can be provided, which can be manually actuated in a simple manner. No screws or other retaining means or fastening elements have to be loosened, at the most an optionally provided retaining ring for axial securing of the first part. The mutual engagement of the components, which is to say of the first part, the stop device(s) and the second part, can be ensured solely based on the gravitational force. The planar mounting on the annular end faces can ensure exact positioning of the components relative to each other and can make the rotatable connection very robust and smooth.

A sliding surface shall preferably be understood to mean a surface that has a low coefficient of friction for sliding friction, either due to particularly low roughness or a particularly smooth surface, or due to a low-friction material having lubricating properties. Zinc diecasting, either with or without coating, can be used as a material for the stop device or the adjusting ring, for example.

The stop device is preferably designed as an adjusting ring having a form-locked contour protruding at the end face in the axial direction toward the second part. An adjusting ring shall preferably be understood to mean a rotationally symmetrical part (apart from any stops), which can be positioned in varying rotational angle positions, such as offset by 15° in each case, which is to say in 24 different rotational angle positions, for example.

The stop device is preferably a single-piece part which can be plugged into the second part in the axial direction and on which the at least one counterstop preferably protrudes in the radial direction, in particular from an outer or inner lateral surface of the stop device. In this way the space requirement can be minimized in the axial direction (the necessary installation height), and a flat design can be implemented.

According to one exemplary embodiment, the adjustable stop mechanism comprises at least two stop devices, which are disposed axially behind each other (in series), wherein each stop device comprises a counterstop protruding in the axial direction. In this way, the stop can be coupled to both counterstops. The counterstops can preferably be disposed so as to overlap in the axial direction. This simplifies the simultaneous coupling or engagement with multiple counterstops. The counterstops are preferably disposed on different pitch circles. Viewed in the radial direction, the counterstops are preferably designed to be at least approximately congruent. This makes a maximum rotational angle possible, which is to say a rotational angle that is not limited by each counterstop of multiple counterstops requiring a certain circular arc for itself. Even when a multitude of stop devices, which is to say even when three or more stop devices, are present, the stop mechanism can then also be set as if only a single stop device were used. This also increases the flexibility and variability of the stop mechanism.

The two counterstops are preferably dimensioned so as to correspond to each other in the axial direction in such a way that a respective free end (in particular an upper edge) of the two counterstops can be disposed in the same axial position. In other words, axially overlapping stop devices or counterstops comprise counterstops, the respective free end of which, or the end face of which, can be disposed in the same axial position, viewed in the axial direction. In this way, the first part can be provided in an advantageous design as a double-walled ring, which surrounds the at least two counterstops in the axial direction, which is to say which can be placed over both counterstops, in particular in the case of a sleek design in the axial direction.

At least one of the two stop devices preferably has an edge that protrudes in the axial direction, which can be used to position, in particular center, the stop devices relative to each other. This simplifies the manual setting and can cause the components to secure each other.

At least one of the two stop devices preferably has an inner lateral surface, which is designed to geometrically correspond to an appropriate surface of the first connection component. In this way, the (respective) stop device can be positioned concentrically, in particular centered, with respect to the first connection component.

According to one exemplary embodiment, one of the stop devices has a form-locked contour on a lower face, wherein the other of the stop devices has a form-locked contour both on an upper face and a lower face. In this way, the other of the stop devices can be axially mounted between the one stop device and the second part as a stop device mounted on an intermediate basis. The form-locked contour on the two sides can allow a certain rotational angle position to be set both with respect to the one stop device and with respect to the second part. The form-locked contours allow a geometric cooperation of the two stop devices. The two form-locked contours are preferably provided in a completely circumferential manner so that a plurality of different rotational angle positions can be flexibly set, wherein a force transmission takes place independently of a particular rotational angle position.

The two stop devices can preferably be plugged into each other in the axial direction in a torsion-proof manner on form-locked contours that are designed so as to geometrically correspond to each other. The form-locked contours are preferably designed in each case in such a way that the two stop devices can be mounted against each other in a plurality of different rotational angle positions in a torsion-proof manner relative to each other.

According to one exemplary embodiment, the form-locked contours are formed in each case as a plurality of symmetrically circumferentially disposed, radially oriented teeth. This makes a plurality of different rotational angle positions possible, in particular at even distances of 7.5°, for example, from each other.

According to one exemplary embodiment, both the form-locked contour of the one stop device and one of the form-locked contours of the other stop device are formed so as to geometrically correspond to a/the form-locked contour of the second part. Without further modifications or additional components, this makes it possible to optionally design the stop mechanism with only one or with two (or even more) stop devices, in particular depending on whether only the range of rotation or additionally a permissible rotational angle is to be set.

The two stop devices preferably have mutually offset counterstops in the radial direction, so that the counterstops in each case can be rotatably disposed on different pitch circles in the different rotational angle positions independently of each other.

According to one exemplary embodiment, the adjustable stop mechanism comprises a retaining device, which can be disposed on the first part and is configured to cooperate with the at least one stop device. In this way securing, in particular axial securing, can be provided in a simple manner, in particular manually and without tools. The first part can be secured on the first connection component by axial securing by way of the retaining device. By axially positioning and securing the at least one stop device relative to the first part by way of the retaining device, it is also possible to secure the axial position of the at least one stop device relative to the second connection component.

The retaining device is preferably designed as a half shell-shaped cap, which can be clipped onto the first part, in particular in the radial direction. A half shell can be handled in a particularly easy manner.

According to one exemplary embodiment, the retaining device is configured to prevent an axial displacement of the at least one stop device relative to the first part. In this way, axial securing can be provided as an option in a simple manner, in particular manually. One of the stop devices can be secured by way of the retaining device, in particular indirectly via the first part, and further stop device can be secured via the axially secured stop device. The first part can be axially secured on the first connection component and prevent a relative axial displacement between the individual components, which is to say between the first part, the stop devices, and the second part as well as between the second part and the second connection component. The retaining device can ensure manual operability of the stop mechanism in a simple manner, in particular in conjunction with one or two further components, which is to say a retaining ring that is axially secured in the first connection component, and optionally also a (spacer) ring which is disposed between the retaining ring and the first part and by way of which an axial play can also be set, for example.

The retaining device is preferably designed as a half shell having a U-shaped cross-sectional profile and has an inner edge, which can be disposed between the first part and the at least one stop device. The half shell preferably surrounds an outer lateral surface of the first part and is itself secured on the first part, in particular in a predefined relative position with respect to the first part. The inner edge can preferably be axially disposed between an upper face of the at least one stop device and a lower face of the first part. So as to improve the retention of the retaining device on the first part, the inner edge can be designed on both sides as legs of the U profile, so that the retaining device can surround the first part in a shell-like manner. Optionally, the inner edge is provided only on a lower face of the retaining device and can be disposed exclusively between the first part and the stop device. The axial securing of the stop device can preferably be ensured in this position.

According to one exemplary embodiment, the adjustable stop mechanism comprises a damping element, in particular made of elastomer material, which corresponds to the second part and/or the at least one stop device, in particular of a form-locked contour of the respective stop device protruding at an end face in the axial direction, the stop device in particular being designed to geometrically correspond to the form-locked contour. It is thus possible to ensure that impact during impingement of the stops on each other is damped, whereby the service life of the rotatable connection can be increased and/or the mounting device, in particular a piece of medical equipment, can be protected. The damping element can prevent the carrier from swinging back or springing back during sudden impingement of the stops against each other. A damping element shall preferably be understood to mean a rubber element having a geometry that is adapted to the respective form-locked contour. The damping element can have the shape of a meander, for example. The damping element can be provided as an insert or jacket on the second part or on the at least one stop device, in particular on a respective form-locked contour.

According to one exemplary embodiment, the rotatable connection comprises an intermediate element, which is disposed between the first part, in particular between the stop device, and the second connection component, viewed in the axial direction, and has at least one form-locked contour for the non-rotatable connection to the at least one stop device or the second connection component, wherein preferably a form-locked contour is provided on each of the two opposing end faces of the intermediate element. In this way, the stop mechanism that is disposed on the two connection components can be designed even more flexibly and can in particular be provided in a simple manner also in the case of cast sleeves. The form-locked contour can ensure that a rotation of further elements, such as a friction ring inner part, is blocked. The intermediate element can also provide advantages with respect to special manufacturing features. In particular, the form-locked contour can be introduced in a simpler manner on the second part, specifically on a ring section of a fork-shaped sleeve. For example, a costly diecasting mold can be dispensed with. The intermediate element can ensure that a draft angle on the sleeve is compensated for in such a way that a support surface oriented perpendicularly to the rotational axis can be provided.

An intermediate element shall preferably be understood to mean an element that can be coupled in a torsion-proof and form-locked manner both to the at least one stop device and to the second part. The intermediate element is an optionally provided, additional part, on which a form-locked contour can be provided in a particularly simple manner, preferably on an end face. The intermediate element can also be provided for manufacturing reasons, for example. The intermediate element can be machined, in particular the form-locked contour(s) can be introduced, in a simple manner. The intermediate element is easy to handle and has easily accessible surfaces. The (respective) form-locked contour is preferably formed by grooves extending in the radial direction. The grooves can extend along the entire intermediate element. Optionally, the grooves can be provided in combination with springs in some sections (as short grooves).

According to one exemplary embodiment, the intermediate element is designed as a disk, in particular an annular disk. The intermediate element can thus be disposed in series with other components around the first connection component. The flat design of the disk can also ensure a small space requirement in the axial direction.

According to one exemplary embodiment, the intermediate element is designed as a wedge having an irregular axial dimension or thickness with respect to the axial direction. The rotatable connection can thus be easily used in conjunction with a cast sleeve, on which a draft angle is provided. The draft angle can be compensated for by way of the wedge shape, so that the two parts or the at least one stop device can be disposed in an axially aligned manner against each other. In other words, the wedge-shaped geometry is configured to compensate for a draft angle of the sleeve.

The above-described object is also achieved by a support system for a mounting device for arrangement in an operating room and for positioning a piece of medical equipment in the operating room, comprising a rotatable connection according to the invention and the first connection component, in particular in the form of a spindle, and the second connection component, in particular in the form of a sleeve.

A support system shall preferably be understood to mean those components of the mounting device which at least partially also assume a function for holding and positioning the piece of medical equipment. The support system can comprise a plurality of preferably rigid arms or carriers, which can each be displaced relative to each other, and a plurality of levers, joints or bearings.

A piece of medical equipment shall preferably be understood to mean a luminaire, a monitor and/or a supply console, by way of which means for supplying a patient and/or instruments for a surgeon and/or light, clean air or other media required in the operating room can be provided. The piece of medical equipment preferably comprises some operating panel and/or some display device for graphically representing patient data, for example.

According to one exemplary embodiment, the second connection component is designed as a fork-shaped sleeve, wherein the at least one stop device and the first part and the second part are disposed between two ring sections of the sleeve on one of the two ring sections, and wherein the second part has a form-locked section, in particular a fork, by way of which the second part can be positioned on the second connection component in a torsion-proof manner, in particular on a rib. The form-locked section can laterally extend radially outward from the second part. In this arrangement, the second part can be easily mounted on the sleeve in a torsion-proof manner. The sleeve itself does not have to be worked, and in particular does not have to be machined, or also does not have to be worked by milling. Additionally, all components remain easily accessible in this arrangement, in particular since the second part is seated on the ring section of the sleeve. This arrangement also provides the option of retrofitting the adjustable stop mechanism in a simple manner, without having to incorporate a form-locked contour in a sleeve, in particular by subsequent machining, such as milling.

According to one exemplary embodiment, the second connection component is designed as a sleeve, in particular as a fork-shaped sleeve, wherein at least the at least one stop device and the second part, and preferably also the first part, are disposed in the sleeve, in particular between two ring sections of the sleeve, preferably in one of the two ring sections. The rotatable connection can furthermore comprise an intermediate element, which is inserted into the sleeve, in particular into one of the two ring sections. In this way a rotatable connection is provided in which at least one stop device is easily accessible, which simplifies the setting of the rotational angle or rotational angle range. The individual components can be easily inserted into the sleeve, in particular from the side in the radial direction. An additional intermediate element can also be inserted into the sleeve, in particular into one of the two ring sections, in particular so as to compensate for a draft angle and/or enable easy or cost-effective production of the form-locked contours. The individual components can also be easily displaced relative to each other in the axial direction so as to set the rotational angle or the range of rotation.

As a result of the intermediate element, it is also possible to ensure a particularly flat design of the rotatable connection in the axial direction, which is advantageous in the case of central axes, for example, which usually already have a significant extension in the axial direction.

The above-described object is also achieved by a mounting device for arrangement in an operating room and for positioning a piece of medical equipment in the operating room, comprising a rotatable connection according to the invention, or the above-described support system comprising the rotatable connection according to the invention.

In one specific embodiment, the mounting device for arrangement in an operating room and for positioning a piece of medical equipment in the operating room comprises a support system comprising at least one carrier, in particular a support arm, a sleeve, which is mounted so as to rotate about a rotational axis on a spindle on a rotatable connection relative to a stationary part of the mounting device or a further carrier of the mounting device, in particular a rotatable connection according to the invention, wherein the rotatable connection comprises an adjustable stop mechanism, which is disposed between the spindle and the sleeve, which is mounted so as to be rotatable about a rotational axis relative to the spindle, and configured to define at least two different relative rotational angles of the sleeve relative to the spindle, or at least two different ranges of rotation, wherein the adjustable stop mechanism comprises:
    a first part in the form of a double-walled stop ring, which is mounted on the spindle in a torsion-proof manner and comprises a stop in the form of a rib; and
    a second part, which is connected to the sleeve in a torsion-proof manner;
wherein the stop ring is rotatably mounted relative to the second part and disposed so as to be axially displaceable relative to the spindle;
wherein the adjustable stop mechanism comprises two adjusting rings, which can be axially displaced in the direction of the rotational axis and each have a counterstop and which are disposed between the two parts, viewed in the axial direction, and cooperate with the two parts, wherein the respective counterstop cooperates with the rib, and wherein the adjusting rings are configured to define the respective different relative rotational angles or ranges of motion by way of the counterstop, and wherein the stop ring overlaps the adjusting rings in the axial direction and surrounds the respective counterstop radially on the inside and outside, in particular by the counterstops being accommodated in a ring cavity of the stop ring. Using such a stop mechanism, it is possible to position the mounting device, in particular the individual carriers, relative to each other in an operating range that can be set in a flexible manner. The counterstop or counterstops can be offset (rotated) on the second part, either relative to each other and/or relative to the second part, so as to together define a single appropriate rotational angle position or individual different rotational angle positions in each case, in particular with respect to a specific arrangement of the mounting device relative to further components in the operating room.

A carrier shall preferably be understood to mean a beam or support arm, which extends in a particular direction and can ensure the desired operating range for the different setpoint positions of the piece of medical equipment, in particular by a rotary motion about a rotatable connection. The carrier can optionally also be pivoted in the height and/or be displaced in a translatory manner in the height. The carrier can also be a telescoping device having an (additional) degree of freedom of movement in the translatory direction along the longitudinal axis of the carrier. The carrier can be formed at least in part by a continuously cast profiled section, for example, in particular a continuously cast aluminum profiled section.

The at least one stop device can be used to define a range of rotation or a value of a rotational angle of the rotatable connection, in particular a reliable relative rotational angle of the two connection components with respect to each other.

The second part is preferably disposed on the carrier, or on one of the carriers, in the region of the rotatable connection. A contour or a stop can be fixed on one of the carriers, whereby the carrier can be positioned in the different rotational angle positions with respect to the other carrier, or with respect to some other stationary part.

The above-described object is also achieved by a method for setting an adjustable stop mechanism of a rotatable connection between two connection components for a mounting device for arrangement in an operating room, wherein the stop mechanism comprises a first part, a second part and at least one stop device having a respective counterstop, wherein the second part is mounted in a torsion-proof manner on a/the second connection component, which is mounted rotatably about a rotational axis, comprising the following steps:
  releasing a form-locked engagement between the at least one stop device and the second part by axial displacement of the first part and of the at least one stop device along the rotational axis and along the first connection component; and
  defining a range of rotation or a relative rotational angle of the connection components relative to each other by the axial re-displacement of the first part, together with the at least one stop device, and form-locked engagement of the at least one stop device in the second part in a changed rotational angle position. In this way, in particular the advantages described in connection with the rotatable connection are obtained.

According to one advantageous embodiment, the method relates to a stop mechanism comprising at least two stop devices, and further comprises the following steps:
  releasing a form-locked engagement between the first part, in particular a stop of the first part, and a/the respective counterstop of the at least two stop devices by axial displacement of the first part relative to the at least two stop devices, in particular in the direction of the rotational axis;
  releasing a form-locked engagement between the at least two stop devices by axial displacement of the stop devices relative to each other; and
  rotating the stop devices, in particular the counterstops, relative to each other and then engaging, in a form-locked manner, the stop devices by axial re-displacement of the stop devices relative to each other, in particular by plugging them into each other, in a changed rotational angle position before the stop devices, or at least one of the stop devices, is again brought into form-locked engagement with the second part. In this way, a rotational angle and a rotational position can be set in a simple manner, in particular with high flexibility and variability of the stop mechanism. Moreover, individual advantages described in connection with the rotatable connection are also obtained.

The invention will be described in more detail in the following figures based on exemplary embodiments. In the drawings.

Figure 7A:
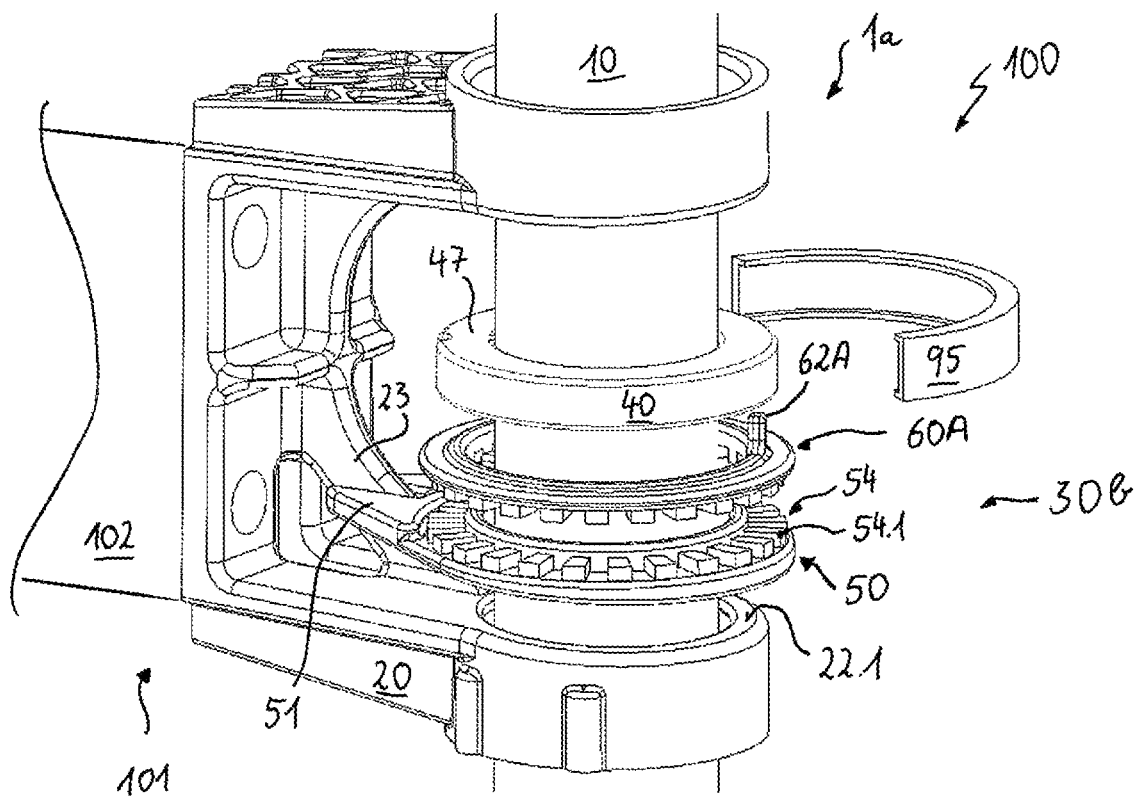
Figure 7B:
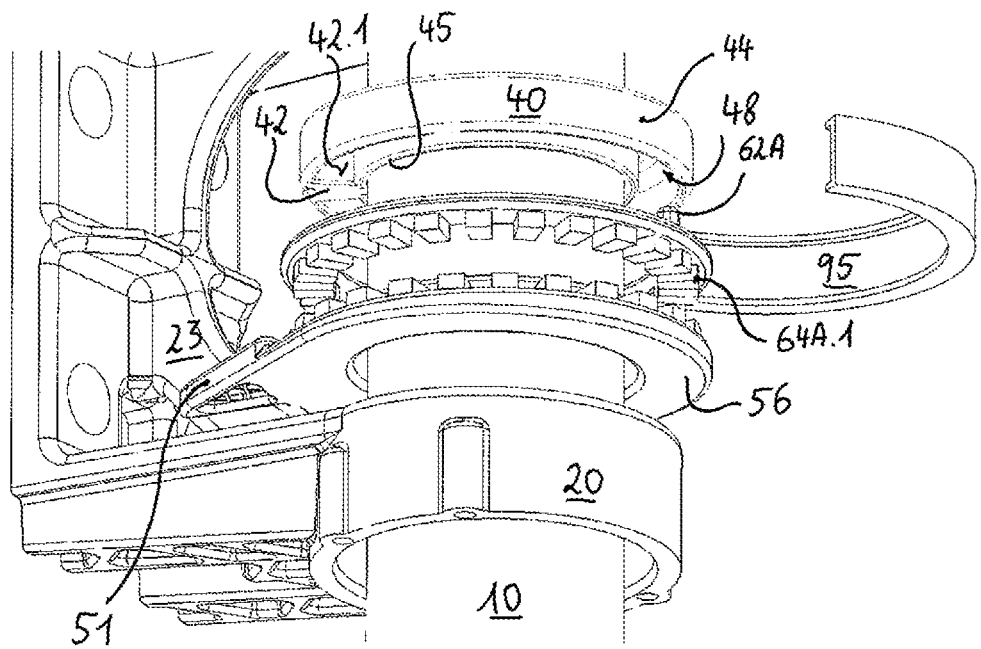
Figure 7C:
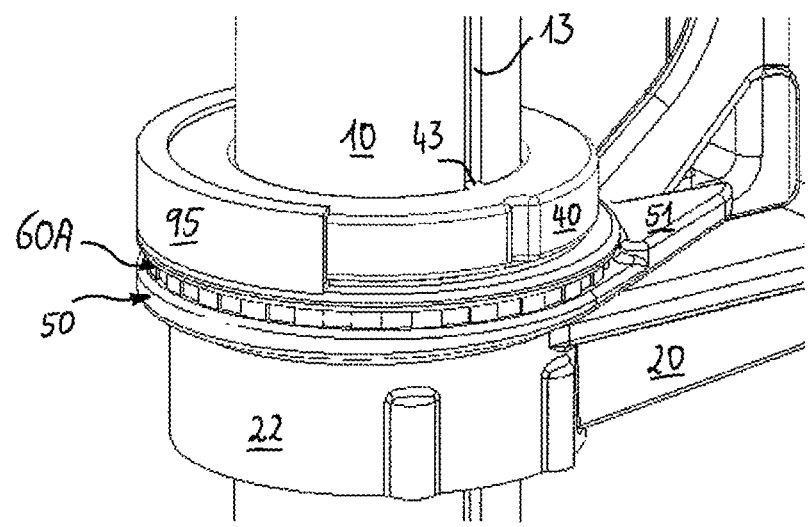
Figure 7D:
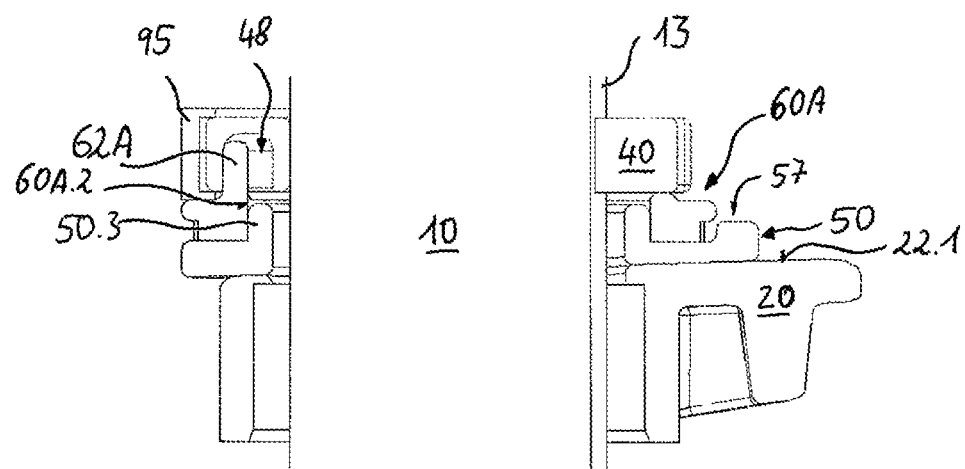
Figure 8A:
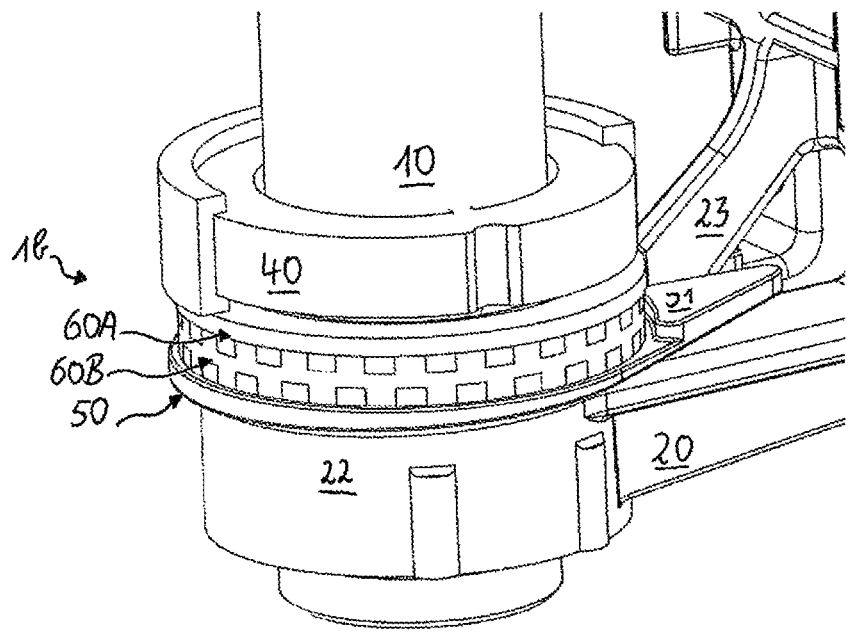
Figure 8B:
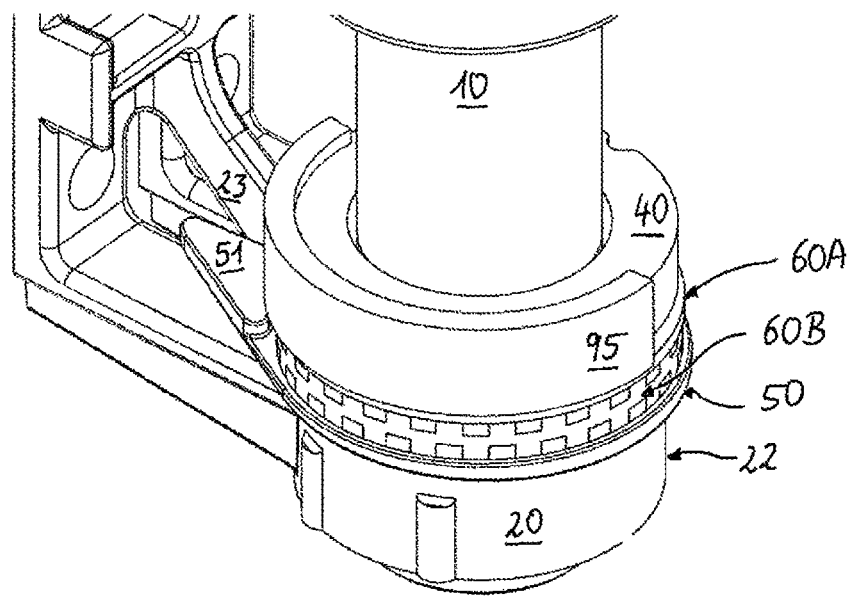

FIGS. 7A, 7B each show a schematic exploded illustration of a perspective view of a rotatable connection according to a further exemplary embodiment of the invention;

FIG. 7C is a perspective view of the rotatable connection shown in FIGS. 7A, 7B when assembled;

FIG. 7D is a sectional view of the rotatable connection shown in FIGS. 7A, 7B, 7C; and FIGS. 8A, 8B each show a schematic illustration of a perspective view of a rotatable connection according to a further exemplary embodiment of the invention.

In connection with the description of the following figures, reference is made to the further figures for some reference numerals, unless they are explicitly described in connection with a particular figure.

Figure 1A:
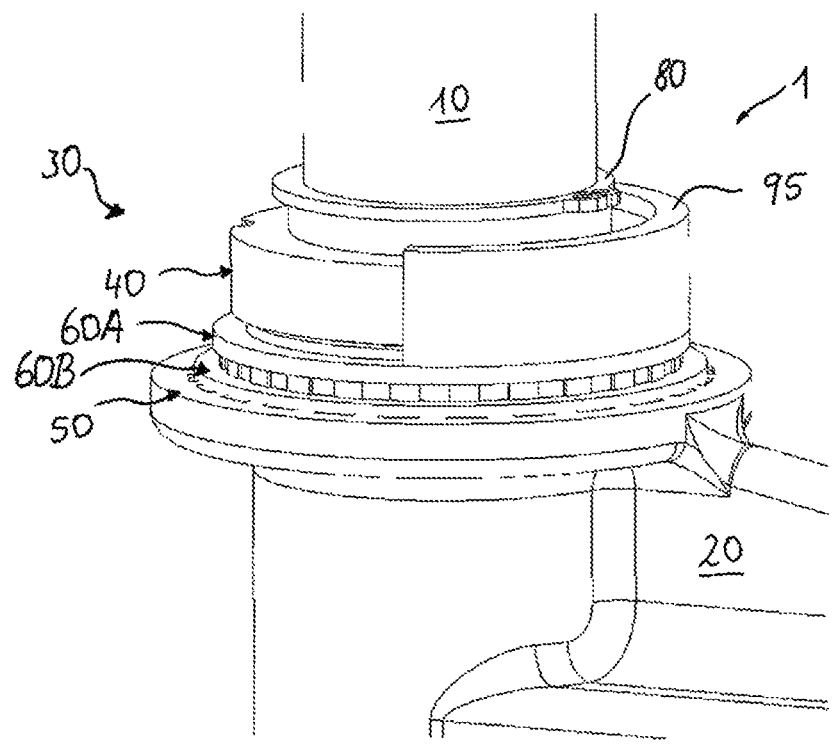
FIG. 1A is a schematic illustration of a perspective view of a rotatable connection according to one exemplary embodiment of the invention.

FIG. 1A shows a rotatable connection 1, which is disposed between a first connection component 10, in particular a spindle, and a second connection component 20, in particular a sleeve. The rotatable connection 1 comprises an adjustable stop mechanism 30 having a first part (stop ring) 40, a first stop device (adjusting ring) 60A, a second stop device (adjusting ring) 60A, and a second part (toothed ring) 50. A retaining ring 80 is mounted on the spindle 10, which can limit or prevent an axial displacement of the stop mechanism 30, in particular in conjunction with a retaining device (half shell or cap) 95.

Figure 1B:
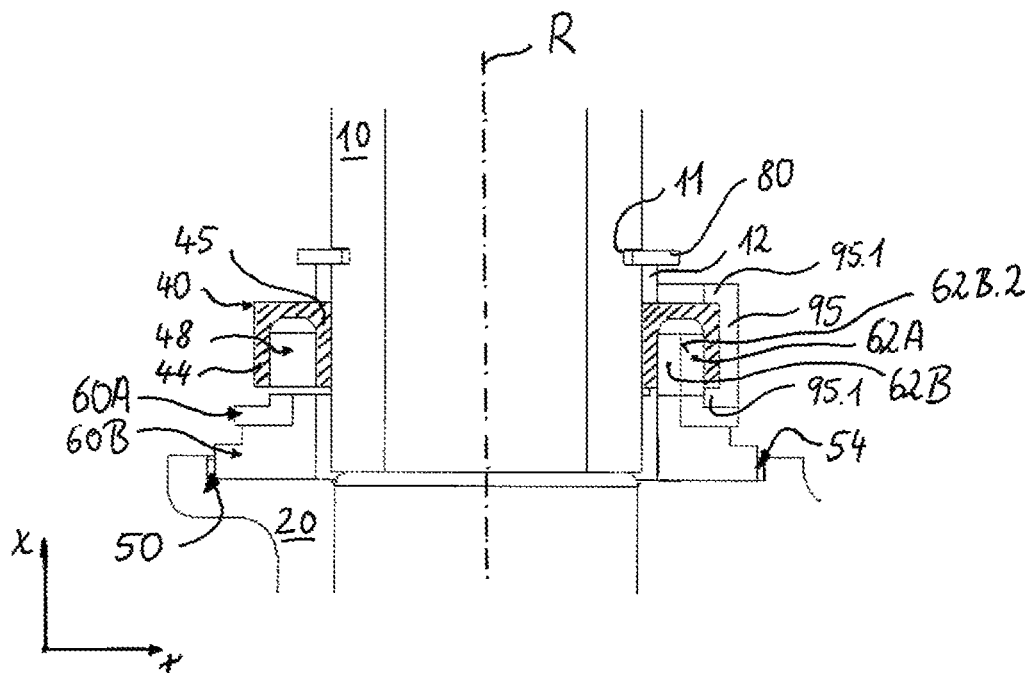
FIG. 1B is a sectional view of the rotatable connection according to the exemplary embodiment shown in FIG. 1A.

The spindle 10 is rotatably disposed about a rotational axis R, as shown in FIG. 1B. A groove 11 for accommodating the retaining ring 80 is provided in the spindle 10. A ring 12 acts axially between the retaining ring 80 and an upper face of the stop ring 40, in particular to optionally axially secure the two adjusting rings 60A, 60B. The stop ring 40 has a U-shaped cross-sectional profile and surrounds a respective counterstop 62A, 62B of the adjusting rings 60A, 60B in the axial direction radially on the inside and outside with an outer wall 44 and an inner wall 45. A ring cavity 48, in which the counterstops 62A, 62B can be disposed in varying rotational angle positions, is formed between the outer wall 44 and the inner wall 45. The two counterstops 62A, 62B overlap each other in the axial direction. An upper free end or an end face of the counterstops 62A, 62B is provided in the same axial position. The counterstops 62A, 62B are disposed directly against each other in the radial direction. An outer surface section 62B.2 of the counterstop 62B of the lower adjusting ring 60B is seated on the inside against a geometrically corresponding inner surface section of the counterstop 62A of the lower adjusting ring 60A. The outer surface section 62B.2 is preferably curved to the outside in a convex manner, in particular corresponding to a radius of a pitch circle on which the outer surface section 62B.2 is disposed.

The adjusting rings 60A, 60B are disposed on top of each other, wherein the lower adjusting ring 60B is seated on the toothed ring 50. The toothed ring 50 is disposed within the sleeve 20 or forms part of the sleeve and can thus (as shown) be formed by the sleeve. A form-locked contour 54 of the toothed ring 50 points in the axial direction to the lower adjusting ring 60B and is designed to geometrically correspond to an appropriate form-locked contour of the lower adjusting ring 60B or also of the upper adjusting ring 60A.

The retaining cap 95 has an inwardly protruding inner edge 95.1 on both sides (top and bottom). The inner edge 95.1 engages radially (which is to say in the direction or counter to the direction of the indicated radial r axis) between the stop ring 40 and the upper adjusting ring 60A and secures the upper adjusting ring 60A against an upward axial displacement, which is to say a displacement in the x direction. The axial securing can be ensured in conjunction with the ring 12. The stop ring 40 can be mounted on the upper adjusting ring 60A by way of the inner edge 95.1 of the retaining cap 95. In addition or as an alternative, the stop ring 40 can also be mounted on an additional projection or sliding element or some other retaining ring, which is axially secured on the spindle 10 or on the sleeve 20, for example. A (respective) adjusting ring is preferably seated against the spindle and is centered via the spindle.

Figure 1C:
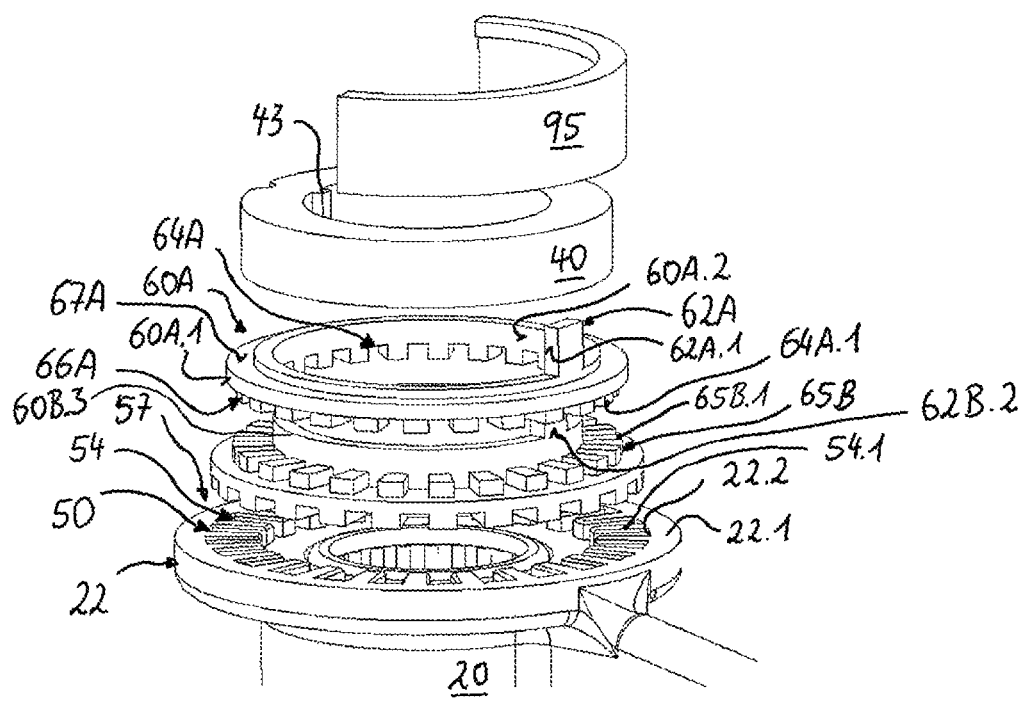
FIG. 1C is a perspective exploded side view of the rotatable connection according to the exemplary embodiment shown in FIG. 1A.

The integrated arrangement of the toothed ring 50 in the sleeve 20 is apparent from FIG. 1C. The sleeve 20 comprises a ring section 22, on which the toothed ring 50 is formed. The ring section has a planar end face 22.1, which forms an upper face 57 of the toothed ring 50. The toothed ring 50 comprises a plurality of teeth 54.1, which extend in the radial direction between an inwardly directed lateral surface 22.2 of the ring section 22 and a passage for the spindle 10. The second adjusting ring 60B can be centered on the lateral surface 22.2.

A lower face 66A of the upper adjusting ring 60A has a form-locked contour 64A, which is formed of individual teeth 64A.1. The form-locked contour 64A is designed to correspond to a form-locked contour 64B having appropriate teeth 64B.1 of the lower adjusting ring 60B. The counterstop of the lower adjusting ring 60B is disposed radially inwardly from the counterstop 62A of the upper adjusting ring 60A. The counterstop 62A of the upper adjusting ring 60A (and accordingly the counterstop of the lower adjusting ring 60B) has a lateral surface (radial side) 62A.1 in the form of a planar stop surface. The upper adjusting ring 60A has an inner lateral surface 60A.2, which can be used to center the upper adjusting ring 60A on the lower adjusting ring 60B. In other words, not only the counterstops or the form-locked contours overlap, but also corresponding lateral surfaces of the adjusting rings.

The upper adjusting ring 60A has an end face or upper face 67A on which an annular surface section is formed, on which the retaining cap 95 can be mounted. The annular surface section preferably has low frictional resistance and can be referred to as a sliding surface or sliding bearing surface, in particular so as to allow a low-resistance relative rotary motion of the retaining cap 95. An outer lateral surface 60A.1 of the upper adjusting ring 60A is preferably disposed on the same pitch circle as an outer lateral surface of the retaining cap 95. This allows a visual inspection to see whether the retaining cap 95 is correctly positioned.

FIG. 1C further shows that the adjustable stop mechanism 30 has a respective form-locked contour on each of four interfaces 57, 66A, 66B, 67B located on the axial end face. The lower adjusting ring 60B has a form-locked contour on both sides.

Figure 2A:
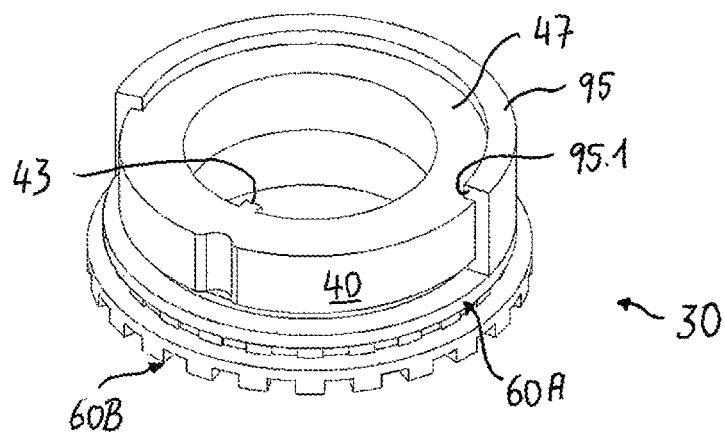
FIG. 2A is a perspective side view of components of an adjustable stop mechanism for a rotatable connection according to the exemplary embodiment shown in FIG. 1A.

FIG. 2A shows the stop ring 40 in a perspective view. The upper inner edge 95.1 of the retaining cap 95 cooperates with an upper face 47 of the stop ring 40. A form-locked element 43, in particular a spring, is disposed on an inner lateral surface of the stop ring 40 and is configured to engage in a corresponding groove of the spindle (not shown; see FIG. 7C). The spring 43 extends in the axial direction along the entire inner lateral surface and ends flush with the upper face 47.

Figure 2B:
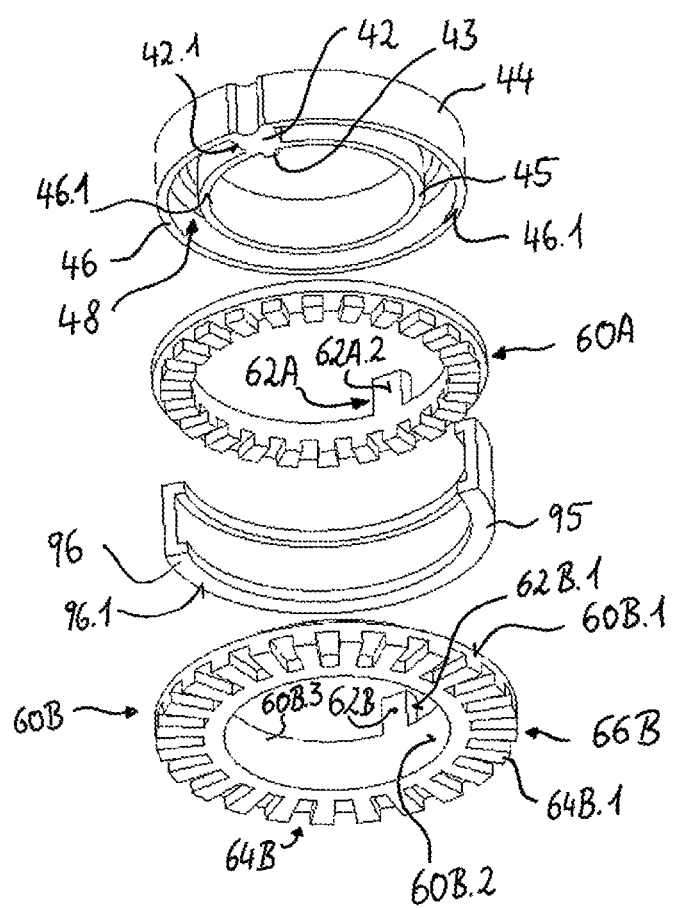
FIG. 2B is a perspective exploded side view of the components of the stop mechanism shown in FIG. 2A.

FIG. 2B shows the stop ring 40 and a/the only stop 42, looking at a lower face 46. The stop 42 has two opposing lateral surfaces 42.1, which are preferably planar and extend in the radial direction. The stop 42 is designed as a partition extending between the walls 44, 45. The stop ring 40 has only a single stop 42. The lateral surfaces 42.1 can also be referred to as radial sides or stop surfaces, which can cooperate with the counterstops 62A, 62B. The counterstop 62A of the upper adjusting ring 60A has a concavely radially outwardly curved inner surface section 62A.2, which can be seated against a corresponding outer surface section of the counterstop 62B of the lower adjusting ring 60B. This arrangement can favor mutual guidance and support of the two adjusting rings against each other, for example, and can also enable a compact design in conjunction with the ring cavity 48. The inner surface section 62A.2 of the counterstop 62A of the upper adjusting ring 60A extends in the axial direction on the same pitch circle as the inner lateral surface of the upper adjusting ring 60A. The inner surface section 62A.2 is a surface section of the inner lateral surface. In this way, the adjusting rings can be disposed inside each other and centered against each other. This embodiment simplifies plugging the adjusting rings into each other.

Two annular surface sections, in particular sliding surfaces 46.1, are provided on the lower face 46 of the stop ring 40, which are associated in each case with one of the walls 44, 45. The sliding surface of the outer wall 44 corresponds to the retaining cap 95, wherein a relative movement does not necessarily have to take place between the retaining cap 95 and the stop ring 40, and the sliding surface of the inner wall 45 can correspond to an optionally providable sliding ring (see FIG. 1B). The retaining cap 95 has a lower face 96, on which an abutment surface, in particular an annular sliding surface 96.1, is formed. This sliding surface 96.1 can become seated against the upper face 67A of the upper adjusting ring 60A.

Like the counterstop of the upper adjusting ring, the counterstop 62B of the lower adjusting ring 60B has a lateral surface (radial side) 62B.1. An inner surface section of the counterstop 62B of the lower adjusting ring 60B extends in the axial direction on the same pitch circle as an inner lateral surface 60B.2 of the lower adjusting ring 60B. The counterstop 62B of the lower adjusting ring 60B extends in the axial direction from an edge 60B.3 protruding in the axial direction. This design allows the adjusting rings 60A, 60B to be plugged into each other in a simple manner. The upper adjusting ring 60A can be pushed along the counterstop 62B and can be pushed over the edge 60B.3. A lower face 66B of the lower adjusting ring 60B has a first form-locked contour 64B, which is formed by teeth 64B.1 that are introduced into the adjusting ring 60B in the radial direction between an outer lateral surface 60B.1 and the lower face 66B.

Figure 3A:
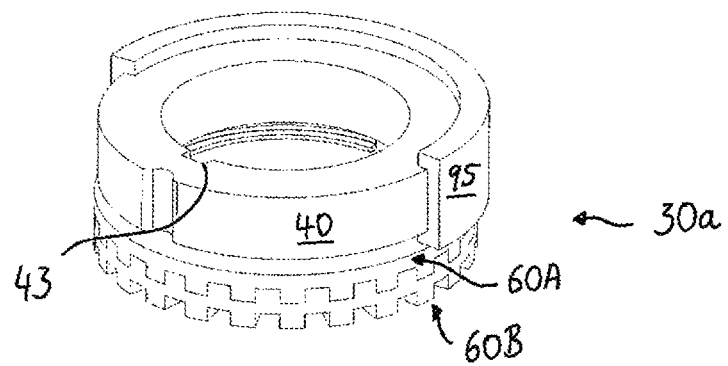
FIG. 3A is a perspective side view of components of an adjustable stop mechanism for a further exemplary embodiment of a rotatable connection according to the invention.
Figure 3B:
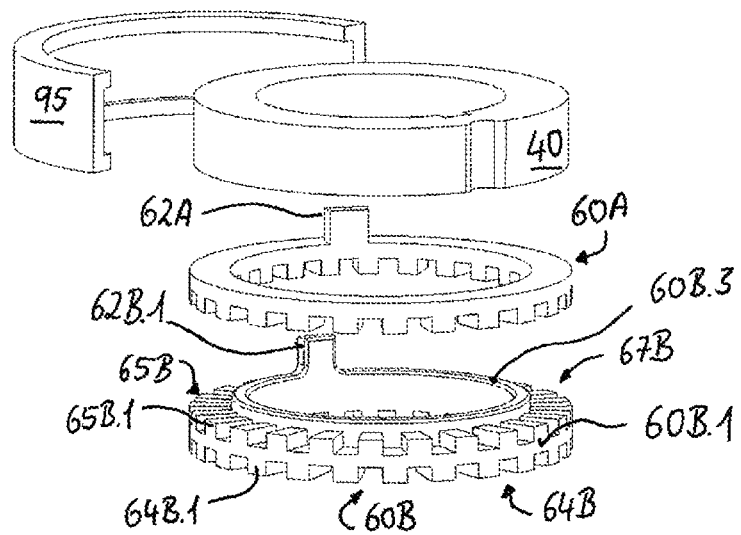
FIG. 3B is a perspective exploded side view of the components of the stop mechanism shown in FIG. 3A.

FIGS. 3A and 3B show another exemplary embodiment of an adjustable stop mechanism 30*a*. The two adjusting rings 60A, 60B each have an outer lateral surface, which are disposed on the same pitch circle. FIG. 3B shows a second form-locked contour 65*b* having individual teeth 65.1, which are provided on an upper face or on an end face section of the lower adjusting ring 60B. The lower adjusting rings shown in the further figures also have such a second form-locked contour, or a form-locked contour that is geometrically modified from the one shown. This exemplary embodiment allows a simple form-locked connection to be provided, which can be used to set fine rotational angles. This exemplary embodiment can be implemented in a simple manner in conjunction with a casting.

Figure 4:
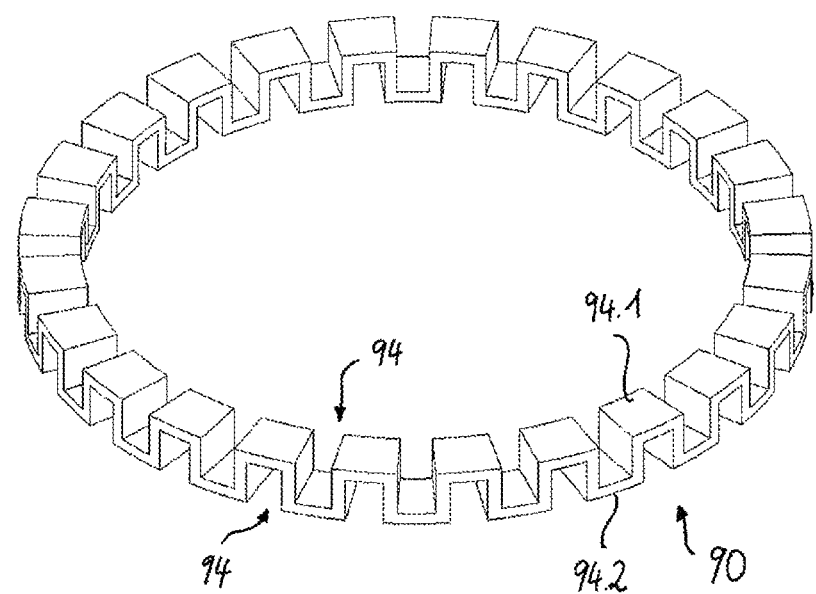
FIG. 4 is a perspective side view of a damping element for a rotatable connection according to one of the exemplary embodiments of the invention.

FIG. 4 shows a damping element 90. The damping element 90 is a rubber element having a geometry that is adapted to the respective form-locked contour of the adjusting rings. The damping element has the shape of a meander. A form-locked contour 94 on the damping element 90 is formed on the two end faces of the damping element 90. The form-locked contour 94 has a tooth geometry in the two axial directions, having teeth 94.1 and 94.2. The form-locked contour 94 is designed in a corresponding fashion to both the form-locked contour of the upper adjusting ring and the second form-locked contour of the lower adjusting ring 60.

Figure 5A:
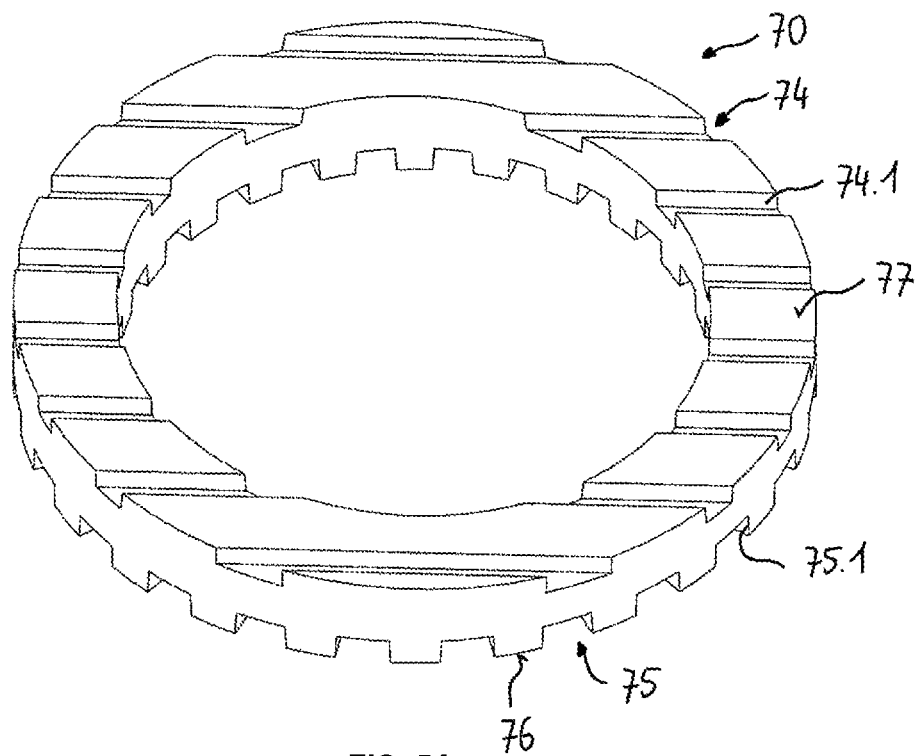
FIG. 5A is a perspective side view of an intermediate element of a rotatable connection according to a further exemplary embodiment of the invention.

FIG. 5A shows an intermediate element 70, which has a first form-locked contour 74 on one end face (as shown, on the upper face) and a second form-locked contour 75 on another end face (as shown, on the lower face). The form-locked contours 74, 75 each have individual grooves 74.1, 75.1. The grooves 75.1 provided on a first end face 76 extend in the radial direction. The grooves 75.1 are preferably provided at a uniform angle with respect to each other, which is to say at a uniform distance from each other, seen in the circumferential direction. The grooves 74.1 provided on a second end face 77 extend in a rectilinear fashion and are preferably oriented parallel to each other. The grooves 74.1 preferably have a uniform distance from each other. The intermediate element 70 has an annular shape, and the end faces 76, 77 are flat or planar. The intermediate element 70 can be described an annular disk.

Figure 5B:
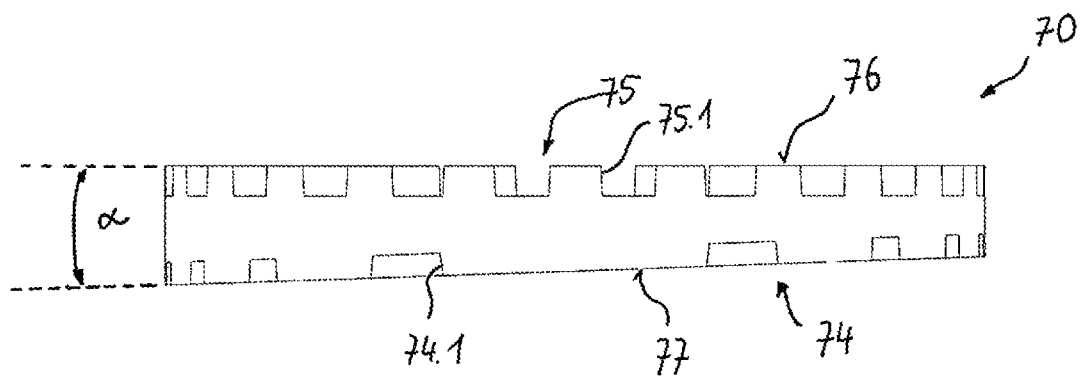
FIG. 5B is a side view of the intermediate element shown in FIG. 5A.

FIG. 5B shows the intermediate element 70 in a side view. It is apparent from FIG. 5B that the first end face 76 is disposed at angle α with respect to the second end face 77, corresponding to the inclination of the draft angle. The angle α is preferably approximately 1.5°. The end faces 76, 77 are not parallel. Rather, the intermediate element 70 has a wedge shape, and in particular it is designed a wedge-shaped annular disk. In this way, a draft angle formed in the sleeve can be compensated for. The end face 76 preferably corresponds to the end face that is urged to engage with the lower adjusting ring.

Figure 6:
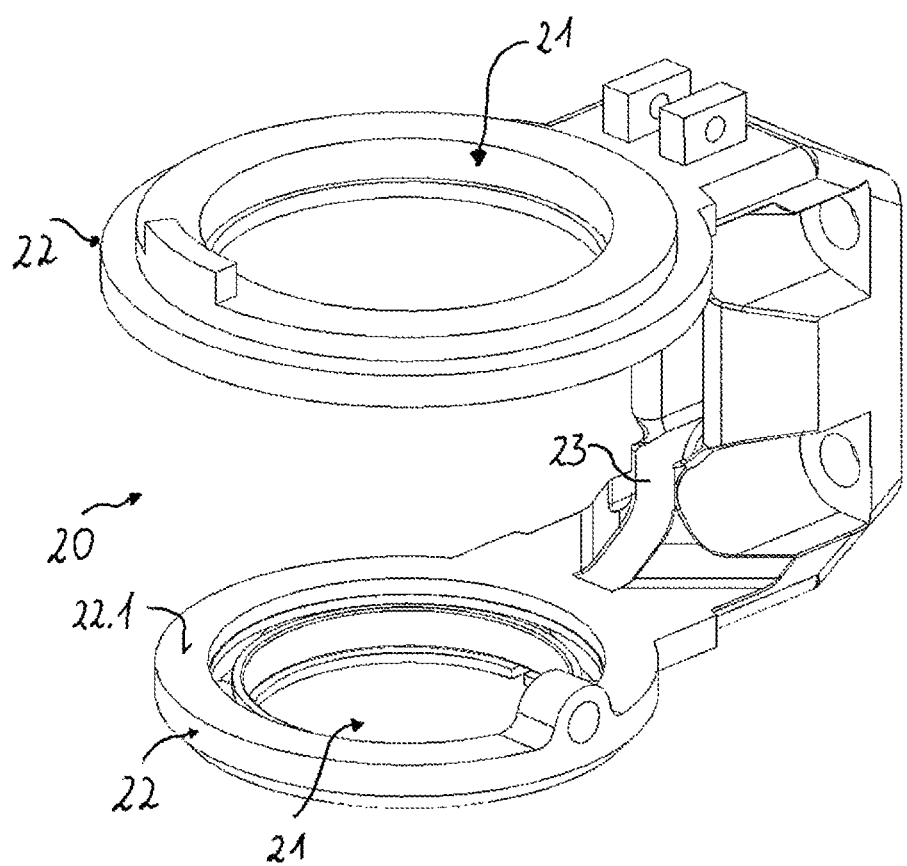
FIG. 6 is a schematic illustration of a perspective view of a fork-shaped sleeve, which is configured for arrangement of a rotatable connection according to one of the exemplary embodiments of the invention.

FIG. 6 shows one embodiment of a fork-shaped sleeve 20. The sleeve 20 has two ring sections 22, on each of which a passage 21 for a spindle is formed. A planar end face 22.1 provides an abutment surface for the second part of the rotatable connection, in particular for a toothed ring (not shown; see FIG. 7A). The sleeve furthermore comprises a rib 23, on which the toothed ring can be positioned in a form-locked manner in a predefined rotational position relative to the sleeve 20.

FIGS. 7A, 7B, 7C and 7D show a further exemplary embodiment of a rotatable connection 1*a* in conjunction with a further exemplary embodiment of an adjustable stop mechanism 30*b*. The rotatable connection 1*a* is provided on a mounting device 100, which comprises a support system 101 having at least one carrier 102. The stop mechanism 30*b* comprises only one adjusting ring 60A, which cooperates with the second part 50 by engagement in the corresponding form-locked contour 54.

The individual components of the stop mechanism 30*b*, in particular the stop ring 40 and the adjusting ring 60A, can cooperate in the same manner as was described in connection with FIGS. 1A to 3B. At each of two interfaces located at the axial end faces, the stop mechanism 30*b* has a form-locked contour and comprises (only) one adjusting ring 60A.

The second part 50 is not integrated into the sleeve 20. The second part 50 rather has a form-locked section 51, here in the form of a fork. The form-locked section 51 surrounds the rib 23 of the sleeve 20 in the radial direction and can thus ensure a torsion-proof arrangement. As is apparent in combination with FIG. 7B, a planar lower face 56, in particular an annular support surface of the second part 50, can be disposed on a planar end face 22.1 of the sleeve 20.

FIG. 7C show the rotatable connection in a set arrangement, wherein the stop ring 40 engages in an anti-rotation element or groove 13 of the spindle 10 by way of the form-locked element 43.

FIG. 7D shows a cross-sectional view of the stop ring 40, the adjusting ring 60A and the toothed ring 50. The stop ring 40 surrounds the counterstop 62A of the adjusting ring 60A. The counterstop 62A is disposed in a ring cavity 48 of the ring 40. An axial displacement of the adjusting ring 60A relative to the toothed ring 50 is prevented by the retaining cap 95, wherein the retaining cap 95 is axially positioned by way of the ring 40. The adjusting ring 60A is centered on an axially protruding edge 50.3 of the toothed ring 50. The toothed ring 50 can optionally be centered on the spindle or on the sleeve.

FIGS. 8A, 8B show a further exemplary embodiment of a rotatable connection 1*b*, which comprises the stop mechanism 30*a* shown in FIGS. 3A, 3B, which is to say two adjusting rings 60A, 60B in conjunction with four interfaces at axial end faces.

Embodiments of the invention relate to a rotatable connection for a mounting device for arrangement in an operating room, comprising an adjustable stop mechanism, which can be disposed between a first connection component and a second connection component, which is mounted rotatably about a rotational axis relative to the first connection, and is configured to define at least two different relative rotational angles of the connection components relative to each other or at least two different ranges or rotation, wherein the adjustable stop mechanism comprises: a first part, which can be mounted on the first connection component in a torsion-proof manner and comprises a stop; and a second part, which can be disposed on the second connection component in a torsion-proof manner, wherein the first part is rotatably mounted relative to the second part, wherein the adjustable stop mechanism comprises at least one stop device having a respective counterstop, which is axially disposed between the two parts, wherein the respective counterstop corresponds to the stop, and wherein the at least one stop device is configured to define the different relative rotational angles or ranges of rotation by way of the respective counterstop. The invention further relates a support system or a mounting device comprising such a rotatable connection, and to a method for setting the adjustable stop mechanism.

LIST OF REFERENCE NUMERALS 1, 1a, 1b rotatable connection
10 first connection component, in particular spindle
11 groove
12 ring
13 anti-rotation element, in particular radial pin or groove in outer lateral surface
20 second connection component, in particular sleeve
21 passage for first connection component
22 ring section of the fork-shaped sleeve
22.1 end face
22.2 inwardly directed lateral surface
23 rib
30, 30a, 30b adjustable stop mechanism
40 first part, in particular double-walled stop ring
42 stop, in particular radial strut, rib or partition
42.1 lateral surface, in particular planar stop surface
43 form-locked element
44 outer wall
45 inner wall, in particular centering element
46 lower face
46.1 abutment surface, in particular annular sliding surface
47 upper face
48 ring cavity (tubular cavity) between the walls
50 second part, in particular toothed ring
50.3 axially protruding edge
51 formed-locked section, in particular fork
54 form-locked contour
54.1 individual tooth
56 planar lower face, in particular annular support surface
57 upper face
60A (first) stop device, in particular (upper) adjusting ring
60A.1 outer lateral surface
60A.2 inner lateral surface
62A counterstop
62A.1 lateral surface (radial side), in particular planar stop surface
62A.2 in particular concavely curved inner surface section
64A form-locked contour
64A.1 individual tooth
66A lower face
67A end face or upper face, in particular annular sliding surface
60B further (second) stop device, in particular (lower) adjusting ring
60B.1 outer lateral surface
60B.2 inner lateral surface
60B.3 axially protruding edge
62B counterstop
62B.1 lateral surface (radial side), in particular planar stop surface
62B.2 in particular convexly curved outer surface section
64B first form-locked contour, in particular on lower face
64B.1 individual tooth
65B second form-locked contour, in particular on upper face
65B.1 individual tooth
66B lower face
67B end face or upper face
70 intermediate element
74 (first) form-locked contour
74.1 individual groove
75 second form-locked contour
75.1 individual groove
76 first end face
77 second end face
80 retaining ring
90 damping element
94 form-locked contour
94.1 individual tooth, in particular on the stop device
94.2 individual tooth, in particular on the second part
95 retaining device, in particular cap
95.1 inner edge (on both sides), in particular leg of a U-shaped profile
96 lower face
96.1 abutment surface, in particular annular sliding surface
100 mounting device
101 support system
102 carrier
R rotational axis
α angle of the two end faces of the intermediate element with respect to each other

The invention claimed is:

1. A rotatable connection for a mounting device, comprising:
an adjustable stop mechanism, which is disposed between a first connection component and a second connection component, wherein the adjustable stop mechanism is mounted about a rotational axis relative to the first connection component, and is configured to define a range of rotation, wherein the first connection component and the second connection component are configured to freely rotate relative to each other in the range of rotation, the adjustable stop mechanism comprising:
a first part, which is mounted on the first connection component in a non-rotatable manner and which comprises a stop;
a second part, which is disposed on the second connection component in a torsion-proof manner, the first part being rotatably mounted relative to the second part;
a first stop device which has a first counterstop and is axially disposed in a torsion-proof manner on the second part between the first part and the second part, the first counterstop corresponding to the stop, the first stop device being configured to adjust the range of rotation by way of the counterstop; and
a second stop device having a second counterstop, wherein the first stop device and the second stop device are disposed axially with one behind the other, wherein the first and second counterstops protrude in the axial direction, and the first and second counterstops are disposed in an overlapping manner in the axial direction, one of the first and second stop devices having a form-locked contour on a lower face, and the other of the first and second stop devices having a respective form-locked contour on an upper face and a lower face.

2. The rotatable connection according to claim 1, further comprising a second stop device having a second counterstop, wherein the first part is configured to couple the stop to at least one of the first counterstop and the second counterstop by axial overlapping, in such a way that the stop either separately cooperates with each of the first counterstop and the second counterstop in individual rotational angle positions, or simultaneously with the first and second counterstops in the same rotational angle position.

3. The rotatable connection according to claim 1, wherein the first part is annular and configured to axially overlap the first counterstop of the first stop device in the axial direction by way of the stop, the first part being designed as a double-walled ring and having a U-shaped cross-sectional profile, and the stop being designed in a form of a rib extending in the radial direction, which connects an inner wall to an outer wall of the ring.

4. The rotatable connection according to claim 1, wherein the adjustable stop mechanism has a respective form-locked contour on each of four interfaces at axial end faces, a component of the adjustable stop mechanism having a form-locked contour on at least two sides.

5. The rotatable connection according to claim 1, wherein the first stop device is disposed in such a way that a torsion-proof arrangement of the first stop device on the second part is ensured by a weight acting on the first stop device.

6. The rotatable connection according to claim 1, wherein the second part has a form-locked contour for defining individual rotational angle positions on an upper face pointing in the axial direction toward the first stop device, and the first stop device has a form-locked contour corresponding thereto on a lower face pointing in the axial direction toward the second part.

7. The rotatable connection according to claim 1, wherein the form-locked contours of the first and second stop devices are designed in each case as a plurality of symmetrically circumferentially disposed, radially oriented teeth.

8. The rotatable connection according to claim 7, wherein both the form-locked contour of the one stop device and one of the form-locked contours of the other stop device are formed so as to geometrically correspond to a form-locked contour of the second part.

9. The rotatable connection according to claim 1, wherein the adjustable stop mechanism comprises a retaining device that includes a half shell-shaped cap, which can be disposed on the first part and is configured to cooperate with the at least one stop device to prevent an axial displacement of the first stop device relative to the first part.

10. The rotatable connection according to claim 1, wherein the adjustable stop mechanism comprises a damping element made of elastomer material, which corresponds to the second part and/or to the first stop device, having a form-locked contour of the respective stop device protruding at the end face in the axial direction.

11. The rotatable connection according to claim 1, wherein the rotatable connection comprises an intermediate element, which is disposed axially between the first part and the second connection component and has at least one form-locked contour for a non-rotatable connection to the first stop device or the second connection component, a respective form-locked contour being provided on each of two opposing end faces of the intermediate element.

12. A mounting device for arrangement in an operating room and for positioning a piece of medical equipment in the operating room, the mounting device comprising the rotatable connection according to claim 1.

13. A method for setting the adjustable stop mechanism of the rotatable connection according to claim 1 the method comprising:
releasing a form-locked engagement between the first stop device and the second part by axial displacement of the first part and of the first stop device along the rotational axis and along the first connection component; and
defining a range of rotation or a relative rotational angle of the connection components relative to each other by axial re-displacement of the first part, together with the first stop device, and form-locked engagement of the first stop device in the second part in a changed rotational angle position.

14. The method according to claim 13, wherein the stop mechanism comprises a second stop device having a second counterstop, further comprising:
releasing a form-locked engagement between the stop of the first part, and the first and second counterstops of the first and second stop devices by axial displacement of the first part relative to the first and second stop devices in the direction of the rotational axis;
releasing a form-locked engagement between the first and second stop devices by axial displacement of the first and second stop devices relative to each other; and
rotating the first and second stop devices including the first and second counterstops, relative to each other and then engaging, in a form-locked manner, the first and second stop devices by axial re-displacement of the first and second stop devices relative to each other by plugging them into each other, in a changed rotational angle position before at least one of the first and second stop devices is again brought into form-locked engagement with the second part.

15. A rotatable connection for a mounting device, comprising:
an adjustable stop mechanism, which is disposed between a first connection component and a second connection component, wherein the adjustable stop mechanism is mounted about a rotational axis relative to the first connection component, and is configured to define a range of rotation, wherein the first connection component and the second connection component are configured to freely rotate relative to each other in the range of rotation, the adjustable stop mechanism comprising:
a first part, which is mounted on the first connection component in a non-rotatable manner and which comprises a stop; and
a second part, which is disposed on the second connection component in a torsion-proof manner, the first part being rotatably mounted relative to the second part;
a first stop device which has a first counterstop and is axially disposed in a torsion-proof manner on the second part between the first part and the second part, the respective counterstop corresponding to the stop, and the first stop device being configured to adjust the ranges of rotation by way of the counterstop
wherein the adjustable stop mechanism comprises a second stop device having a second counterstop, wherein the first stop device and the second stop device are disposed axially with one behind the other, wherein the first and second counterstops protrude in the axial direction, and the first and second counterstops are disposed in an overlapping manner in the axial direction, one of the first and second stop devices having a form-locked contour on a lower face, and the other of the first and second stop devices having a respective form-locked contour on an upper face and a lower face, the form-locked contours of the first and second stop devices being designed in each case as a plurality of symmetrically circumferentially disposed, radially oriented teeth.

16. A rotatable connection for a mounting device, comprising:
an adjustable stop mechanism, which is disposed between a first connection component and a second connection component, wherein the adjustable stop mechanism is mounted about a rotational axis relative to the first connection component, and is configured to define a range of rotation, wherein the first connection component and the second connection component are configured to freely rotate relative to each other in the range of rotation, the adjustable stop mechanism comprising:
- a first part, which is mounted on the first connection component in a non-rotatable manner and which comprises a stop; and
- a second part, which is disposed on the second connection component in a torsion-proof manner, the first part being rotatably mounted relative to the second part;
- a first stop device which has a first counterstop and is axially disposed in a torsion-proof manner on the second part between the first part and the second part, the respective counterstop corresponding to the stop, and the first stop device being configured to adjust the ranges of rotation by way of the counterstop
- wherein the adjustable stop mechanism comprises a retaining device that includes a half shell-shaped cap, which can be disposed on the first part and is configured to cooperate with the at least one stop device to prevent an axial displacement of the first stop device relative to the first part.

17. A rotatable connection for a mounting device, comprising:
- an adjustable stop mechanism, which is disposed between a first connection component and a second connection component, wherein the adjustable stop mechanism is mounted about a rotational axis relative to the first connection component, and is configured to define a range of rotation, wherein the first connection component and the second connection component are configured to freely rotate relative to each other in the range of rotation, the adjustable stop mechanism comprising:
- a first part, which is mounted on the first connection component in a non-rotatable manner and which comprises a stop; and
- a second part, which is disposed on the second connection component in a torsion-proof manner, the first part being rotatably mounted relative to the second part;
- a first stop device which has a first counterstop and is axially disposed in a torsion-proof manner on the second part between the first part and the second part, the respective counterstop corresponding to the stop, and the first stop device being configured to adjust the ranges of rotation by way of the counterstop
- wherein the rotatable connection comprises an intermediate element, which is disposed axially between the first part and the second connection component and has at least one form-locked contour for the non-rotatable connection to the first stop device or the second connection component, a respective form-locked contour being provided on each of two opposing end faces of the intermediate element.

* * * * *